(12) United States Patent
Empedocles et al.

(10) Patent No.: US 9,228,948 B2
(45) Date of Patent: *Jan. 5, 2016

(54) SPATIAL POSITIONING OF SPECTRALLY LABELED BEADS

(71) Applicant: LIFE TECHNOLOGIES CORPORATION, Carlsbad, CA (US)

(72) Inventors: Stephen Empedocles, Mountain View, CA (US); Andrew Watson, Lexington, MA (US); Jian Jin, Berkeley, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/700,248

(22) Filed: Apr. 30, 2015

(65) Prior Publication Data

US 2015/0247801 A1 Sep. 3, 2015

Related U.S. Application Data

(63) Continuation of application No. 13/777,032, filed on Feb. 26, 2013, now Pat. No. 9,046,477, which is a continuation of application No. 12/620,475, filed on Nov. 17, 2009, now Pat. No. 8,405,828, which is a continuation of application No. 11/425,851, filed on Jun. 22, 2006, now abandoned, which is a continuation of application No. 09/827,256, filed on Apr. 5, 2001, now Pat. No. 7,079,241.

(60) Provisional application No. 60/195,520, filed on Apr. 6, 2000.

(51) Int. Cl.
*G01N 21/25* (2006.01)
*G01N 21/27* (2006.01)
(Continued)

(52) U.S. Cl.
CPC .......... *G01N 21/6428* (2013.01); *B01L 3/5025* (2013.01); *B01L 3/5085* (2013.01); *B01L 3/502715* (2013.01); *B01L 3/502761* (2013.01); *G01N 21/25* (2013.01); *G01N 21/253* (2013.01); *G01N 21/274* (2013.01); *G01N 21/278* (2013.01); *G01N 21/6452* (2013.01); *G01N 21/6486* (2013.01); *G01N 21/6489* (2013.01); *G01N 33/54373* (2013.01); *B01J 2219/005* (2013.01); *B01J 2219/00317* (2013.01); *B01J 2219/00432* (2013.01); *B01J 2219/00574* (2013.01); *B01J 2219/00576* (2013.01); *B01J 2219/00578* (2013.01);
(Continued)

(58) Field of Classification Search
None
See application file for complete search history.

(56) References Cited

U.S. PATENT DOCUMENTS 3,473,027 A 10/1969 Freeman et al.
3,628,016 A 12/1971 Berier
(Continued)

FOREIGN PATENT DOCUMENTS

EP 0667398 A2 8/1995
EP 0990903 4/2000
(Continued)

OTHER PUBLICATIONS 01928376.1, "Office Action Mailed Mar. 4, 2010", 84.
(Continued)

*Primary Examiner* — Gordon J Stock, Jr.
(74) *Attorney, Agent, or Firm* — Life Technologies Corporation

(57) ABSTRACT

Devices, systems, kits, and methods for detecting and/or identifying a plurality of spectrally labeled bodies well-suited for performing multiplexed assays. By spectrally labeling the beads with materials which generate identifiable spectra, a plurality of beads may be identified within the fluid. Reading of the beads is facilitated by restraining the beads in arrays, and/or using a focused laser.

21 Claims, 9 Drawing Sheets

(51) Int. Cl.
| | | |
|---|---|---|
| *G01N 21/64* | (2006.01) | |
| *B01L 3/00* | (2006.01) | |
| *G01N 33/543* | (2006.01) | |
| *B82Y 30/00* | (2011.01) | |
| *C40B 40/06* | (2006.01) | |
| *C40B 60/14* | (2006.01) | |
| *G01N 15/00* | (2006.01) | |
| *G01N 15/14* | (2006.01) | |
| *G01N 35/00* | (2006.01) | |

(52) U.S. Cl.
CPC ............... *B01J 2219/00585* (2013.01); *B01J 2219/00596* (2013.01); *B01J 2219/00648* (2013.01); *B01J 2219/00657* (2013.01); *B01J 2219/00659* (2013.01); *B01J 2219/00677* (2013.01); *B01J 2219/00707* (2013.01); *B01J 2219/00722* (2013.01); *B01J 2219/00743* (2013.01); *B01L 3/545* (2013.01); *B01L 2200/0668* (2013.01); *B01L 2300/021* (2013.01); *B01L 2300/0819* (2013.01); *B01L 2300/0829* (2013.01); *B01L 2400/0454* (2013.01); *B01L 2400/0457* (2013.01); *B82Y 30/00* (2013.01); *C40B 40/06* (2013.01); *C40B 60/14* (2013.01); *G01N 21/6456* (2013.01); *G01N 2015/0092* (2013.01); *G01N 2015/1472* (2013.01); *G01N 2015/1497* (2013.01); *G01N 2021/6441* (2013.01); *G01N 2021/6482* (2013.01); *G01N 2035/00158* (2013.01); *G01N 2035/00742* (2013.01); *G01N 2035/00752* (2013.01); *G01N 2201/04* (2013.01)

(56) References Cited

U.S. PATENT DOCUMENTS

| | | | |
|---|---|---|---|
| 3,663,813 A | 5/1972 | Shaw | |
| 4,485,308 A | 11/1984 | Rabatin | |
| 4,560,286 A | 12/1985 | Wickersheim | |
| 5,079,169 A | 1/1992 | Chu et al. | |
| 5,377,003 A | 12/1994 | Lewis et al. | |
| 5,427,779 A | 6/1995 | Elsner et al. | |
| 5,460,831 A | 10/1995 | Kossovsky et al. | |
| 5,483,338 A | 1/1996 | Wachter et al. | |
| 5,495,334 A | 2/1996 | Nagoshi et al. | |
| 5,512,745 A | 4/1996 | Finer et al. | |
| 5,525,798 A | 6/1996 | Berson et al. | |
| 5,537,000 A | 7/1996 | Alivisatos et al. | |
| 5,543,158 A | 8/1996 | Gref et al. | |
| 5,620,857 A | 4/1997 | Weetall et al. | |
| 5,631,141 A | 5/1997 | Sonek et al. | |
| 5,665,582 A | 9/1997 | Kausch et al. | |
| 5,751,018 A | 5/1998 | Alivisatos et al. | |
| 5,776,674 A | 7/1998 | Ulmer | |
| 5,786,219 A | 7/1998 | Zhang et al. | |
| 5,807,522 A | 9/1998 | Brown et al. | |
| 5,932,139 A | 8/1999 | Oshima et al. | |
| 5,939,021 A | 8/1999 | Hansen et al. | |
| 5,958,782 A | 9/1999 | Bentsen et al. | |
| 5,990,476 A | 11/1999 | Larson et al. | |
| 5,990,479 A | 11/1999 | Weiss et al. | |
| 5,993,634 A * | 11/1999 | Simpson et al. ............... 204/612 |
| 6,024,925 A | 2/2000 | Little et al. | |
| 6,054,325 A | 4/2000 | Kedar | |
| 6,055,106 A | 4/2000 | Grier et al. | |
| 6,057,103 A | 5/2000 | Short | |
| 6,066,459 A | 5/2000 | Garini et al. | |
| 6,108,463 A | 8/2000 | Herron et al. | |
| 6,139,831 A | 10/2000 | Shivashankar et al. | |
| 6,159,749 A | 12/2000 | Liu | |
| 6,180,415 B1 | 1/2001 | Schultz et al. | |
| 6,207,392 B1 | 3/2001 | Weiss et al. | |
| 6,225,198 B1 | 5/2001 | Alivisatos et al. | |
| 6,235,540 B1 | 5/2001 | Siiman et al. | |
| 6,236,945 B1 | 5/2001 | Simpson et al. | |
| 6,252,664 B1 | 6/2001 | Barbera-Guillem et al. | |
| 6,253,104 B1 | 6/2001 | Jo | |
| 6,263,104 B1 | 7/2001 | McGrew | |
| 6,274,320 B1 | 8/2001 | Rothberg et al. | |
| 6,274,323 B1 | 8/2001 | Bruchez et al. | |
| 6,274,873 B1 | 8/2001 | Outwater et al. | |
| 6,284,465 B1 | 9/2001 | Wolber | |
| 6,288,220 B1 | 9/2001 | Kambara et al. | |
| 6,294,343 B1 | 9/2001 | Mack et al. | |
| 6,296,810 B1 | 10/2001 | Ulmer et al. | |
| 6,297,018 B1 | 10/2001 | French et al. | |
| 6,306,610 B1 | 10/2001 | Bawendi et al. | |
| 6,309,701 B1 | 10/2001 | Barbera-Guillem | |
| 6,319,426 B1 | 11/2001 | Bawendi et al. | |
| 6,322,901 B1 | 11/2001 | Bawendi et al. | |
| 6,326,144 B1 | 12/2001 | Bawendi et al. | |
| 6,333,110 B1 | 12/2001 | Barbera-Guillem | |
| 6,384,409 B1 | 5/2002 | Libbey et al. | |
| 6,388,788 B1 * | 5/2002 | Harris et al. ............... 359/196.1 |
| 6,468,808 B1 * | 10/2002 | Nie et al. ............... 436/524 |
| 6,492,125 B2 | 12/2002 | Kauvar et al. | |
| 6,500,622 B2 | 12/2002 | Bruchez, Jr. et al. | |
| 6,528,165 B2 * | 3/2003 | Chandler ............... 428/402.2 |
| 6,544,732 B1 | 4/2003 | Chee et al. | |
| 6,548,171 B1 | 4/2003 | Barbera-Guilem et al. | |
| 6,602,671 B1 | 8/2003 | Bawendi et al. | |
| 6,617,583 B1 | 9/2003 | Bawendi et al. | |
| 6,624,940 B1 | 9/2003 | Grier et al. | |
| 6,632,655 B1 | 10/2003 | Mehta et al. | |
| 6,720,411 B2 * | 4/2004 | Mirkin et al. ............... 536/23.1 |
| 6,734,420 B2 | 5/2004 | Empedocles et al. | |
| 6,759,235 B2 | 7/2004 | Empedocles et al. | |
| 7,033,754 B2 | 4/2006 | Chee et al. | |
| 7,079,241 B2 | 7/2006 | Empedocles et al. | |
| 7,115,884 B1 * | 10/2006 | Walt et al. ............... 250/459.1 |
| 7,559,481 B2 | 7/2009 | Empedocles et al. | |
| 7,799,558 B1 * | 9/2010 | Dultz ............... 435/287.2 |
| 8,219,327 B2 | 7/2012 | Nova et al. | |
| 8,360,321 B2 * | 1/2013 | Lee et al. ............... 235/468 |
| 8,405,828 B2 | 3/2013 | Empedocles et al. | |
| 8,741,630 B2 | 6/2014 | Dickinson et al. | |
| 9,046,477 B2 * | 6/2015 | Empedocles et al. ............... 21/25 |
| 2001/0029049 A1 | 10/2001 | Walt et al. | |
| 2001/0055764 A1 | 12/2001 | Empedocles et al. | |
| 2002/0004246 A1 | 1/2002 | Daniels et al. | |
| 2002/0028457 A1 | 3/2002 | Empedocles et al. | |
| 2002/0090650 A1 | 7/2002 | Empedocles et al. | |
| 2003/0036096 A1 | 2/2003 | Ravkin et al. | |
| 2003/0099940 A1 | 5/2003 | Empedocles et al. | |
| 2003/0148544 A1 * | 8/2003 | Nie et al. ............... 436/524 |
| 2003/0157504 A1 * | 8/2003 | Chee et al. ............... 435/6 |
| 2004/0132122 A1 * | 7/2004 | Banerjee et al. ............... 435/7.92 |
| 2005/0069956 A1 | 3/2005 | Seul | |
| 2006/0244963 A1 | 11/2006 | Empedocles et al. | |
| 2009/0176221 A1 | 7/2009 | Bruchez et al. | |

FOREIGN PATENT DOCUMENTS

| | | |
|---|---|---|
| JP | 9506166 | 6/1997 |
| WO | 94/08221 | 4/1994 |
| WO | 95/08107 | 3/1995 |
| WO | 99/26299 | 5/1999 |
| WO | 99/50916 | 10/1999 |
| WO | 99/52708 | 10/1999 |
| WO | 99/67639 | 12/1999 |
| WO | 00/06980 | 2/2000 |
| WO | 00/14545 | 3/2000 |
| WO | 00/16087 | 3/2000 |
| WO | 00/17103 | 3/2000 |
| WO | 00/17642 | 3/2000 |
| WO | 00/65094 | 11/2000 |

(56) References Cited

FOREIGN PATENT DOCUMENTS

| WO | 00/68692 | 11/2000 |
|---|---|---|
| WO | 01/61040 | 8/2001 |
| WO | 01/61348 | 8/2001 |

OTHER PUBLICATIONS 01928376.1, "Response to Mar. 4, 2010 Office Action mailed" Filed on Jul. 14, 2010.
U.S. Appl. No. 09/827,013, "Notice of Allowance mailed Dec. 24, 2003".
U.S. Appl. No. 09/827,013, "Office Action mailed Mar. 10, 2003".
U.S. Appl. No. 09/827,013, "Office Action mailed Sep. 8, 2003".
U.S. Appl. No. 09/827,013, "Response to Mar. 10, 2003 Office Action", Filed Jun. 10, 2003.
U.S. Appl. No. 09/827,013, "Response to Sep. 8, 2003 Office Action", Filed Dec. 1, 2003.
U.S. Appl. No. 09/827,076, "Draft Response to Oct. 3, 2002 Office Action for Discussion", Filed Feb. 13, 2003.
U.S. Appl. No. 09/827,076, "Notice of Allowance", Feb. 13, 2004.
U.S. Appl. No. 09/827,076, "Office Action mailed Feb. 21, 2003".
U.S. Appl. No. 09/827,076, "Office Action mailed Mar. 29, 2002".
U.S. Appl. No. 09/827,076, "Office Action mailed May 9, 2003".
U.S. Appl. No. 09/827,076, "Office Action mailed Oct. 3, 2002".
U.S. Appl. No. 09/827,076, "Office Action mailed Nov. 17, 2003".
U.S. Appl. No. 09/827,076, "Response to Feb. 21, 2003 Office Action", Filed Mar. 3, 2003.
U.S. Appl. No. 09/827,076, "Response to Mar. 29, 2002 Office Action", Filed Jun. 28, 2002.
U.S. Appl. No. 09/827,076, "Response to May 9, 2003 Office Action", Filed Aug. 11, 2003.
U.S. Appl. No. 09/827,076, "Response to Nov. 17, 2003 Office Action", Filed Jan. 12, 2004.
U.S. Appl. No. 09/827,076, "Response to Restriction Req.", Filed Dec. 19, 2001.
U.S. Appl. No. 09/827,076 "Restriction Requirement mailed Nov. 6, 2001".
U.S. Appl. No. 09/827,256, "Notice of Allowance mailed Jan. 30, 2006".
U.S. Appl. No. 09/827,256, "Office Action mailed May 6, 2004".
U.S. Appl. No. 09/827,256, "Office Action mailed May 18, 2005".
U.S. Appl. No. 09/827,256, "Office Action mailed Oct. 1, 2003".
U.S. Appl. No. 09/827,256, "Office Action mailed Nov. 16, 2004".
U.S. Appl. No. 09/827,256, "Response to May 6, 2004 Office Action", Filed Aug. 4, 2004.
U.S. Appl. No. 09/827,256, "Response to May 18, 2005 Office Action", Filed Aug. 2, 2005.
U.S. Appl. No. 09/827,256, "Response to Oct. 1, 2003 Office Action", Filed Dec. 30, 2003.
U.S. Appl. No. 09/827,256, "Response to Nov. 16, 2004 Office Action", Filed Feb. 16, 2005.
U.S. Appl. No. 09/999,780, "Notice to File Missing Parts mailed Dec. 13, 2001".
U.S. Appl. No. 09/999,780, "Office Action mailed Dec. 20, 2004".
U.S. Appl. No. 09/999,780, "Office Action mailed Dec. 3, 2002".
U.S. Appl. No. 09/999,780, "Preliminary Amendment filed May 1, 2002".
U.S. Appl. No. 09/999,780, "Supplementary Amendment filed in response to Examiner Interview", Filed on Nov. 1, 2004.
U.S. Appl. No. 10/807,616, "Final Office Action issued Sep. 24, 2008".
U.S. Appl. No. 10/807,616, "Final Rejection", mailed Sep. 24, 2008.
U.S. Appl. No. 10/807,616, "Non-Final Office Action mailed Dec. 20, 2007".
U.S. Appl. No. 10/807,616, "Notice of Allowance issued May 27, 2009", 13 pgs.
U.S. Appl. No. 10/807,616, "Response to Dec. 20, 2007 Office Action", Filed Jun. 20, 2008.
U.S. Appl. No. 10/832,635, "Final Office Action mailed Jul. 21, 2008", 1-9.
U.S. Appl. No. 10/832,635, "Non-Final Office Action", received for U.S. Appl. No. 10/832,635 mailed on Mar. 12, 2007, 1-11.
U.S. Appl. No. 10/832,635, "Non-Final Office Action mailed Apr. 9, 2009", 12 pgs.
U.S. Appl. No. 10/832,635, "Response to Notice of Non-Compliant Amendment", Filed Feb. 22, 2008, 1-6.
U.S. Appl. No. 10/832,635, "Response to Restriction Requirement", received for U.S. Appl. No. 10/832,635, filed Oct. 13, 2006, 1-6.
U.S. Appl. No. 10/832,635, "Restriction Requirement received", for U.S. Appl. No. 10/832,635 mailed on Sep. 13, 2006, 1-6.
10177052.7, "Extended European Search Report mailed Jan. 28, 2011".
10180073.8, "Extended European Search Report Mailed Mar. 11, 2011".
U.S. Appl. No. 11/425,851, "Non-Final Office Action Mailed on Nov. 14, 2008", 1-12.
U.S. Appl. No. 11/425,851, "Office Action mailed Aug. 18, 2009", 13 pgs.
U.S. Appl. No. 11/425,851, "Office Action mailed Jan. 14, 2008".
U.S. Appl. No. 11/425,851, "Office action mailed Oct. 4, 2007".
U.S. Appl. No. 11/425,851, "Response to Jan. 14, 2008 OA", mailed Jul. 14, 2008.
U.S. Appl. No. 11/425,851, "Response to Oct. 4, 2007 OA", mailed Oct. 24, 2007.
U.S. Appl. No. 12/620,475, "Office Action Mailed Sep. 1, 2010", 12.
2,403,601, "Office action mailed Mar. 11, 2010".
2,405,267, "Office Action mailed on Jul. 16, 2009".
2,405,267, "Response to Jul. 16, 2009 Office Action Mailed", Filed on Jan. 12, 2011, 12.
2001-574483, "Office Action Mailed Jun. 13, 2011", 8.
2001-575029, "Office Action Mailed Jun. 13, 2011".
2403601, "Response to Mar. 11, 2010 Office Action Mailed" Filed on Sep. 13, 2010, 16.
U.S. Appl. No. 60/195,520, "Method for Encoding Material with Semiconductor Nanocrystals, Compositions made thereby and Devices for Detection and Decoding Thereof", Apr. 6, 2000.
Alivisatos, A. P., "Perspectives on the Physical Chemistry of Semiconductor Nanocrystals", *The Journal of Physical Chemistry*, vol. 100, No. 31, 1996, 13226-13239.
Ashkin, "The pressure of laser light", *Scientific American*, vol. 226, No. 2, Feb. 1972, 63-71.
Ashkin, Arthur, "Acceleration and Trapping of Particles by Radiation Pressure", *Physical Review Letters*, vol. 24, No. 4, Jan. 26, 1970, 156-159.
Ashkin, Arthur, "Inaugural Article: Optical trapping and manipulation of neutral particles using lasers", *Proceedings of the National Academy of Sciences (PNAS)*, vol. 94, No. 10, May 13, 1997, 4853-4860.
Aue, W. P. et al., "Two-dimensional Spectroscopy. Application to Nuclear Magnetic Resonance", *The Journal of Chemical Physics*, vol. 64, No. 5, Mar. 1, 1976, 2229-2246.
Brenan, Colin J. et al., "Chemical imaging with a confocal scanning Fourier-transform-Raman microscope", *Applied Optics*, vol. 33, No. 31, 1994, 7520-7528.
Bruchez Jr., et al., "Semiconductor Nanocrystals as Fluorescent Biological Labels", *Science*, vol. 281, No. 5385, Sep. 25, 1998, 2013-2016.
Chan, et al., "Quantum Dot Bioconjugates for Ultrasensitive Nonisotopic Detection" *Science*, vol. 281, No. 5385, 1998, pp. 2016-2018.
Colarusso, Pina et al., "Infrared Spectroscopic Imaging: From Planetary to Cellular Systems", *Applied Spectroscopy*, vol. 52, No. 3, Mar. 1998, 106A-120A(15).
Colvin, V. L. et al., "Semiconductor Nanocrystals Covalently Bound to Metal Surfaces with Self-Assembled Monolayers", *Journal of the American Chemical Society*, vol. 114, No. 13, 1992, 5221-5230.
Dabbousi, B. O. et al., "(Cdse)Zns Core-Shell Quantum Dots: Synthesis and Characterizations of a Size Series of Highly Luminescent Nanocrystallites", *J. Phys. Chem. B*, vol. 101, No. 46, Jun. 26, 1997, 9463-9475.

(56) References Cited

OTHER PUBLICATIONS

Danek, Michal et al., "Synthesis of Luminescent Thin-Film CdSe/ZnSe Quantum dot composites Using CdSe Quantum Dots Passivated with an Overlayer of ZnSe", *Chemistry of Materials*, vol. 8, No. 1, 1996, 173-180.
Empedocles, Stephen A. et al., "Photoluminescence from Single Semiconductor Nanostructures", vol. 11, No. 15, *Advanced Materials*, Oct. 20, 1999, 1243-1256.
Empedocles, Stephen A. et al., "Photoluminescence Spectroscopy of Single CdSe Nanocrystallite Quantum Dots", *Physical Review Letters*, vol. 77, No. 18, Oct. 28, 1996, 3873-3876.
EP 01923207, "European Search Report mailed on Dec. 22, 2005", 3.
EP 01923207, "Examination Report mailed Apr. 19, 2006".
EP 01923207, "Examination Report mailed Jun. 29, 2007".
EP 01923207, "Examination Report mailed Jul. 9, 2008".
EP 01923207, "Response to Jul. 9, 2009 Office Action", filed on Feb. 16, 2009.
EP 01928376, "EP Search Report mailed on Dec. 22, 2005", 3.
EP 01928376, "Examination Report mailed Apr. 19, 2006", 1-5.
EP 01928376, "Examination Report mailed Jul. 2, 2007", 1-4.
EP 01928376, "Examination Report mailed Jul. 9, 2008", 1-5.
EP 01928376, "Response to Jul. 9, 2008 Office Action", Filed on Feb. 16, 2009.
Fateley, W. G. et al., "Application of a Two-Dimensional Hadamard Encoding Mask for the Imaging of Thin-Layer Chromatography Plates by Laser-Induced Fluorescence or Surface-Enhanced Raman Scattering and for Use with a Photoacoustic Detector to Generate Three-Dimensional Photoacou", *Applied Spectroscopy*, vol. 47, No. 9, 1993, 1464-1470.
Goldman, E. et al., "An Algorithmically Optimized Combinatorial Library Screened by Digital Imaging Spectroscopy", *Bio/Technology*, vol. 10, 1992, pp. 1557-1561.
Guzelian, A. A. et al., "Synthesis of Size-Selected, Surface Passivated InP Nanocrystals", *The Journal of Physical Chemistry A*, vol. 100, No. 17, 1996, 7212-7219.
Hammaker, R M. et al., "Multi-dimensional Hadamard transform spectrometry", *Journal of Molecular Structure*, vol. 348, Mar. 15, 1995, 135-138.
Helmerson, Kristian et al., "Optical tweezers-based immunosensor detects femtomolar concentrations of antigens", *Clinical Chemistry*, vol. 43, No. 2, Feb. 1997, 379-383.
Hines, Margaret A. et al., "Synthesis and Characterization of Strongly Luminescing ZnS-Capped CdSe Nanocrystals", *J. Phys. Chem.*, vol. 100, No. 2, 1996, 468-471.
Katari, J.E. B. et al., "X-ray Photoelectron Spectroscopy of CdSe Nanocrystals with Applications to Studies of the Nanocrystal Surface", *The Journal of Physical Chemistry A*, vol. 98, No. 15,, 1994, 4109-4117.
Kraan, J. et al., "Setting up and calibration of a flow cytometer for multicolor immunophenotyping", *J. Biol regul Homeost Agents*, 17, 2003, 223-233.
Kuno, M et al., "The band edge luminescence of surface modified CdSe nanocrystallites: Probing the luminescing state", *Journal of Chemical Physics*, vol. 106, No. 23,, 1997, 9869-9882.
Lakowicz, Joseph R. et al., "Ch 1: Introduction to Fluoresence", *Principles of Fluorescence Spectroscopy—Second Edition*, 1999, 1-4.
Malik, Z et al., "Fourier transform multipixel spectroscopy for quantitative cytology", *Journal of Microscopy*, vol. 182, No. 2, May 1996, 133-140.

Mei, et al., *Journal of Analytical Chemistry*, vol. 354, 1996, 250.
Morris, Hannah R. et al., "Imaging Spectrometers for Fluorescence and Raman Microscopy: Acousto-Optic and Liquid Crystal Tunable Filters" *Journal of the Society for Applied Spectroscopy*, vol. 48, No. 7, Jul. 1994, 857-866.
Mortensen, A N. et al., "A Hadamard-multiplexed spectrometer based on an acousto-optic tunable filter", *IEEE Transactions on Instrumentation and Measurement*, vol. 45, No. 2, Apr. 1996, 394-398.
Murray, C. B. et al., "Synthesis and characterization of nearly monodisperse CdE (E = sulfur, selenium, tellurium) semiconductor nanocrystallites", *Journal of the American Chemical Society*, vol. 115, No. 19, 1993, 8706-8715.
Peng, Xiaogang et al., "Epitaxial Growth of Highly Luminescent CdSe/CdS Core/Shell Nanocrystals with Photostability and Electronic Accessibility", *J. Am. Chem. Soc.*, vol. 119, No. 30, 1997, 7019-7029.
Perfetto, Stephen et al., "Quality assurance for polychromatic flow cytometry", *Nature Protocols*, co. 1, No. 3, 2006, 1522-1530.
Press, William H. et al., "Numerical Recipes in C: The Art of Scientific Computing", (*Textbook*), Cambridge University Press, 1996, 1-994.
Quake, Stephen R. et al., "The dynamics of partially extended single molecules of DNA", *Nature*, vol. 388, Jul. 10, 1997, 151-154.
Royal Society of Chemistry, "IUPAC Compendium of Chemical Terminology", http://goldbook.iupac.org/, Site as quoted was: <http://www.chemsoc.org/cgi-shell/empower.exe, Chembytes Infozone> Updated May 10, 1998. This site no longer available., May 10, 1998, 1-5.
Sachleben, Joseph R. et al., "NMR Studies of the Surface Structure and Dynamics of Semiconductor Nanocrystals", *Chemical Physics Letters*, vol. 198, No. 5, Oct. 16, 1992, 431-436.
Seveus, et al., *Cytometry*, vol. 13, 1992, 329-338.
Steigerwald, M. L. et al., "Surface Derivatization and Isolation of Semiconductor Cluster Molecules", *Journal of the American Chemical Society*, vol. 110, No. 10, 1988, 3046-3050.
Treado, Patrick J. et al., "A thousand points of light: the Hadamard transform in chemical analysis and instrumentation", *Analytical Chemistry*, vol. 61, No. 11, Jun. 1, 1989, 723A-734A.
Treado, Patrick J. et al., "Hadamard Transform Raman Microscopy of Laser-Modified Graphite Electrodes", *Journal of the Society for Applied Spectroscopy*, vol. 44, No. 8, 1990, 1270-1275.
Treado, Patrick J. et al., "Multichannel Hadamard Transform Raman Microscopy", *Journal of the Society for Applied Spectroscopy*, vol. 44, No. 1, 1990, 1-4.
Turner, John F. et al., "Near-Infrared Acousto-Optic Tunable Filter Hadamard Transform Spectroscopy", *Journal of the Society for Applied Spectroscopy*, vol. 50, No. 2, Feb. 1996, 277-284.
Veinot, Jonathan G. et al., "Surface Functionalization of Cadium Sulfide Quantum-Confined Nanoclusters. 3. Formation and Derivatives of a Surface Phenolic Quantum Dot", *Chem. Mater.*, vol. 9, No. 10, Oct. 16, 1997, 2117-2122.
Wegrzyn, Jeff et al., "Unintensified Photodiode Array Fluorescence Detector for High-Performance Liquid Chromatography", *Analytical Chemistry*, vol. 62, No. 17, Sep. 1, 1990, 1754-1756.
WO 2001/077391 "PCT ISR", Jun. 27, 2001.
WO 2001/077678 "PCT ISR", Oct. 18, 2001.
WO 2001/078288 "PCT ISR", Dec. 17, 2001.
Youvan, Douglas C., "Imaging sequence space", *Nature*, vol. 369, May 5, 1994, 79-80.

* cited by examiner

SPATIAL POSITIONING OF SPECTRALLY LABELED BEADS

CROSS-REFERENCE TO RELATED APPLICATIONS

This application is a continuation of U.S. application Ser. No. 13/777,032 filed Feb. 26, 2013, which is a continuation of U.S. application Ser. No. 12/620,475, filed Nov. 17, 2009, now U.S. Pat. No. 8,405,828, which is a continuation of U.S. application Ser. No. 11/425,851, filed Jun. 22, 2006, abandoned, which claims the benefit of priority and is a continuation of U.S. Non-Provisional application Ser. No. 09/827,256 filed Apr. 5, 2001, now U.S. Pat. No. 7,079,241 and U.S. Provisional Patent Application No. 60/195,520 entitled "Method for Encoding Materials with Semiconductor Nanocrystals, Compositions Made Thereby, and Devices for Detection and Decoding Thereof," filed Apr. 6, 2000, the full disclosures of which are incorporated herein by reference.

The subject matter of the present application is related to the following co-pending patent applications, the disclosures of which are also incorporated herein by reference: U.S. patent application Ser. No. 09/160,458 filed Sep. 24, 1998 and entitled, "Inventory Control"; U.S. patent application Ser. No. 09/397,432 filed Sep. 17, 1999, and also entitled "inventory Control"; PCT Patent Application No. WO 99/50916 as published on Apr. 1, 1999, entitled "Quantum Dot White and Colored Light Emitting Diodes"; and U.S. patent application Ser. No. 09/259,982 filed Mar. 1, 1999, and entitled "Semiconductor Nanocrystal Probes for Biological Applications and Process for Making and Using Such Probes". All other references cited herein are also incorporated by reference.

BACKGROUND OF THE INVENTION

The present invention generally provides devices, compositions of matter, kits, systems, and methods for detecting and identifying a plurality of spectrally labeled bodies. In a particular embodiment, the invention provides systems and methods for detecting and identifying a plurality of spectral codes generated by such bodies, especially for measuring the results of high-throughput bead-based assay systems, and the like. The invention will often use labeled beads which generate identifiable spectra that include a number of discreet signals having measurable characteristics, such as wavelength and/or intensity.

Tracking the locations and/or identities of a large number of items can be challenging in many settings. Barcode technology in general, and the Universal Product Code in particular, has provided huge benefits for tracking a variety of objects. Barcode technologies often use a linear array of elements printed either directly on an object or on labels which may be affixed to the object. These barcode elements often comprise bars and spaces, with the bars having varying widths to represent strings of binary ones, and the spaces between the bars having varying widths to represent strings of binary zeros.

Barcodes can be detected optically using devices such as scanning laser beams or handheld wands. Similar barcode schemes can be implemented in magnetic media. The scanning systems often electro-optically decode the label to determine multiple alphanumerical characters that are intended to be descriptive of (or otherwise identify) the article or its character. These barcodes are often presented in digital form as an input to a data processing system, for example, for use in point-of-sale processing, inventory control, and the like.

Barcode techniques such as the Universal Product Code have gained wide acceptance, and a variety of higher density alternatives also have been proposed. Unfortunately, these standard barcodes are often unsuitable for labeling many "libraries" or groupings of elements. For example, small items such as jewelry or minute electrical components may lack sufficient surface area for convenient attachment of the barcode. Similarly, emerging technologies such as combinatorial chemistry, genomics research, microfluidics, potential pharmaceutical screening, micromachines, and other nanoscale technologies do not appear well-suited for supporting known, relatively large-scale barcode labels. In many of these developing fields, it is often desirable to make use of large numbers of compounds within a fluid, and identifying and tracking the movements of such fluids using existing barcodes is particularly problematic. While a few chemical encoding systems for chemicals and fluids have been proposed, reliable and accurate labeling of large numbers of small and/or fluid elements remains a challenge.

Small scale and fluid labeling capabilities have recently advanced radically with the suggested application of semiconductor nanocrystals (also known as C-Dot™ particles), as detailed in U.S. patent application Ser. No. 09/397,432, the full disclosure of which is incorporated herein by reference. Semiconductor nanocrystals are microscopic particles having size-dependent optical and/or electromagnetic emission properties. As the band gap energy of such semiconductor nanocrystals vary with a size, coating and/or material of the crystal, populations of these crystals can be produced having a variety of spectral emission characteristics. Furthermore, the intensity of the emission of a particular wavelength can be varied, thereby enabling the use of a variety of encoding schemes. A spectral label defined by a combination of semiconductor nanocrystals having differing emission signals can be identified from the characteristics of the spectrum emitted by the label when the semiconductor nanocrystals are energized.

A particularly promising application for semiconductor nanocrystals is in multiplexed and/or high-throughput assay systems. Multiplexed assay formats would be highly desirable for improved throughput capability, and to match the demands that combinatorial chemistry is putting on established discovery and validation systems for pharmaceuticals. For example, simultaneous elucidation of complex protein patterns may allow detection of rare events or conditions, such as cancer. In addition, the ever-expanding repertoire of genomic information would benefit from very efficient, parallel and inexpensive assay formats. Desirable multiplexed assay characteristics may include ease of use, reliability of results, a high-throughput format, and extremely fast and inexpensive assay development and execution.

A number of known assay formats may currently be employed for high-throughput testing. Each of these formats has limitations, however. By far the most dominant high-throughput technique is based on the separation of different assays into different regions of space. The 96-well plate format is the workhorse in this arena.

In 96-well plate assays, the individual wells (which are isolated from each other by walls) are often charged with different components, and the assay is performed and then the assay result in each well measured. The information about which assay is being run is carried with the well number or the position on the plate, and the result at the given position determines which assays are positive. These assays can be based on chemiluminescence, scintillation, fluorescence, scattering, or absorbance/colorimetric measurements, and the details of the detection scheme depend on the reaction being assayed.

Multi-well assays have been reduced in size to enhance throughput, for example, to accommodate 384 or 1536 wells per plate. Unfortunately, the fluid delivery and evaporation of the assay solution at this scale are significantly more confounding to the assays. High-throughput formats based on multi-well arraying often rely on complex robotics and fluid dispensing systems to function optimally. The dispensing of the appropriate solutions to the appropriate bins on the plate poses a challenge from both an efficiency and a contamination standpoint, and pains must be taken to optimize the fluidics for both properties. Furthermore, the throughput is ultimately limited by the number of wells that one can put adjacent on a plate, and the volume of each well. Arbitrarily small wells may have arbitrarily small volumes, resulting in a signal that scales with the volume, shrinking proportionally with the cube of the radius. Nonetheless the spatial isolation of each well, and thereby each assay, has been much more common than running multiple assays in a single well. Such single-well multiplexing techniques are not widely used, due in large part to the difficulty in "demultiplexing" or resolving the results of the different assays in a single well.

For even higher throughput genomic and genetic analysis techniques, positional array technology has been shrunk to microscopic scales, often using high-density oligonucleotide arrays. Over a 1-cm square of glass, tens to hundreds of thousands of different nucleotides can be written in, for example, 25-.mu.m spots, which are well resolved from each other. On this planar test structure or "chip," which is emblazoned with an alignment grid, a particular spot's x,y position determines which oligonucleotide is present at that spot. Typically 3'- or 5'-labeled amplified DNA is added to the array, hybridized and is then detected using fluorescence-based techniques. Although this is a very powerful technique for assaying a large number of genetic markers simultaneously, the cost is still very high, and the flexibility of this assay is limited.

Once the masks have been written for the photolithographic process that builds the particular DNA sequences into a particular location on the chip, they are fixed and the addition thereto of new markers comes at a very high price. The extremely small feature size, and the highly parallel assay format, comes at the cost of the flexibility inherent in a common platform system such as the 96-well plates. In addition, the assay is ultimately performed at the surface of the chip, and the results depend on the kinetics of the hybridization to the surface, a process that is negatively influenced by steric issues and diffusion issues. In fact, small microarray chips are not particularly suited to the detection of rare events, as the diffusion of the solution over the chip may not be sufficiently thorough. In order to perform the hybridizations to the microarray chips more efficiently, a dedicated fluidics workstation can be used to pump the solution over the surface of the chip repeatedly; such instruments add cost and time to execution of the assay.

The use of spectral barcodes holds great promise for enhancing the throughput of assays, as described in an application entitled "Semiconductor Nanocrystal Probes for Biological Applications and Process for Making and Using such Probes," U.S. application Ser. No. 09/259,982 filed Mar. 1, 1999, the full disclosure of which is incorporated herein by reference. Multiplexed assays may be performed using a number of probes which include both a spectral label (often in the form of several semiconductor nanocrystals) and one or more moieties. The moieties may be capable of selectively bonding to one or more detectable substances within a sample fluid, while the spectral labels can be used to identify the probe within the fluid (and hence the associated moiety). As the individual probes can be quite small, and as the number of spectral codes which can be independently identified can be quite large, large numbers of individual assays might be performed within a single fluid sample by including a large number of differing probes. These probes may take the form of quite small beads, with each bead optionally including a spectral label, a moiety, and a bead body or matrix, often in the form of a polymer. The reaction times and rare event identification accuracy of such beads may be quite advantageous, particularly when the beads are free-floating within a fluid, without being affixed to a surface.

Together with their substantial advantages, there will be significant challenges in implementing multiplexed, spectrally encoded bead-based assay techniques. In particular, determining multiplexed assay results by accurately reading each spectral barcode and/or assay result from within a fluid may prove quite problematic.

In light of the above, it would generally be desirable to provide improved systems and methods for sensing and identifying signal generating bodies. It would be particularly beneficial if these improved techniques facilitated the identification of a plurality of spectral codes generated by bodies disposed within and/or exposed to a fluid. To take advantage of the potential capabilities of spectral coding of multiplexed assay probes, it would be highly desirable if these enhanced techniques allowed detection and/or identification of large numbers of spectral codes and/or other signals in a repeatably, highly time efficient manner, while providing improved flexibility, ease of use, rare event/condition detection, and/or accuracy.

SUMMARY OF THE INVENTION

The present invention generally provides improved devices, systems, kits, and methods for detecting and/or identifying a plurality of spectrally labeled bodies. The invention is particularly well-suited for identifying particulate probes or "beads" which have been released in a fluid so as to perform a multiplexed assay. These beads can be quite small and may have differing analytical properties, so that their identification may be problematic if standard inventory systems are applied. By spectrally labeling the beads (for example, by including materials which generate identifiable spectra associated with a bead of a particular type in response to an excitation energy), a plurality of beads may be identified within the fluid. Such spectral labels may, for example, comprise a plurality of differing markers (such as semiconductor nanocrystals, Raman scattering materials, or the like), with the differing markers each generating an identifiable signal, and the combined signals for each type of probe defining the overall spectrum. These spectrally labeled beads have a wide range of applications, and are particularly beneficial for use in multiplexed assay systems.

The techniques of the present invention will often involve spatially positioning or restraining spectrally labeled bodies such as beads. The beads may be dynamically restrained by "sweeping" the fluid with an energy beam such as a focused laser used as an optical tweezers. Alternatively, a plurality of beads may be spatially restrained within an array of openings. Regardless, it will often be advantageous to optically image the restrained bead using an optical train having a spectral dispersion element, such as a prism, a refractive grating, a transmissive grating, or the like.

In a first aspect, the invention provides a spectral label identification method comprising spatially restraining a first spectrally labeled body. A first spectrum is generated from the first body while the first body is spatially restrained. The first spectrum is dispersed across a sensor surface, and the first body is identified from the first dispersed spectrum.

The spectrum generating step will often be performed by at least one semiconductor nanocrystal, often by a plurality of semiconductor nanocrystals, and preferably by a plurality of differing semiconductor nanocrystal populations. Each semiconductor nanocrystal (or population thereof) can act as a marker generating a signal having clearly defined signal characteristics. The combination of these differing markers can define the label, with the differing signals combining to define the overall spectrum. When used as assay probes, spectrally encoded bodies may also include a moiety such as a selective affinity molecule, a member of a binding pair, or the like. The presence or absence of the spectrally encoded body may comprise an assay result signal, or an additional assay signal may be generated by interaction of the moiety with an identifiable substance. Typically, a plurality of spectrally labeled bodies are released in a fluid, and the first body is spatially separated from the other released bodies when the first spectrum is generated. Ideally, a plurality of bodies are spatially restrained as an array in which the bodies are separated from each other to facilitate identification.

In many embodiments, a plurality of spectra from the bodies are simultaneously dispersed across the sensor surface. An array of sites may be spaced to avoid excessive overlap of the dispersed spectra so that each of the bodies can be identified from the associated spectrum. In some embodiments, the spectra may be sensed sequentially with a scanning system by moving a sensor field between the bodies. Such sequential scanning may be used while simultaneously spatially positioning a plurality of bodies, and/or by sequentially restraining the bodies.

The bodies may be restrained within openings in a support structure, with the openings sized as to accommodate a single body. This can inhibit confusion by avoiding generating signals with two bodies which are in (or near) contact. In some embodiments, the bodies may be drawn into the openings from the fluids by pumping fluid into the openings. This allows the bodies to be scanned in a fixed array configuration, and then expelled to make room for a subsequent array. In alternative embodiments, the labeled bodies may be sequentially spatially restrained by an energy beam, such as by a focused laser beam using optical tweezing techniques.

In many embodiments, assay signals may also be sensed from the bodies, the assay signals indicating results of an assay associated with the bodies. Multiplexed assays using these techniques may make use of about 100 different bodies which can be independently identified from their associated spectra, with very highly multiplexed assays often including at least 1,000 different bodies, optionally being 10,000 different bodies.

In another aspect, the invention provides a method comprising spatially restraining a plurality of spectrally labeled bodies so as to define an array. A spectrally dispersed image of the array of bodies is directed onto a sensor to sense spectra generated by the bodies. The bodies are identified from the spectra sensed by the sensor.

The bodies may be restrained within an array of openings affixed in a multi-well plate. The array of bodies may optionally be drawn into the array of openings by drawing fluid into the openings. The bodies may also be expelled from the openings by expelling fluid from the openings. Another array of bodies may then be drawn into the openings by again drawing fluid into the openings. In other embodiments, the bodies may be restrained in the array by an array of discreet binding sites. The binding sites may comprise a material capable of binding to the bodies. Suitable binding materials may comprise a nonspecific "sticky" or adhesive material, a member of a binding pair (with the other member affixed to the body), a selective affinity molecule which selectively binds to one or more particular bodies, or the like. Regardless of whether the array is defined by openings or binding sites, the array will preferably be arranged so as to inhibit the presence of more than a single body at the sites of the array.

In another aspect, the invention provides a method comprising releasing a plurality of bodies in a fluid. A first body is spatially restrained within the fluid by transmitting restraining energy through the fluid toward the body. A first spectrum is generated from the spatially restrained first body, and the first body is identified from the first spectrum.

The spatially restraining step may be preformed with a focused laser beam, particularly when the laser beam is used as an optical tweezers. The focused laser beam may be sized and configured to restrain a single body. For example, optical tweezers have a "trap" with a size determined at least in part by the geometry of the focus laser beam. Where a size of the spectrally labeled body is at least about half the size of the trap, the presence of a plurality of beads within the trap will be inhibited by spatial interference between the beads.

In some embodiments, the focused laser beam may be configured to restrain a plurality of the bodies simultaneously. For example, the trap may be elongated so as to restrain the bodies along a line. This may be accomplished by focusing the laser beam along a line segment.

In some embodiments, a separate excitation energy may be directed toward the restrained body, with the body generating the spectrum in response to the excitation energy. An alternative embodiments, the restrained body may generate a spectrum in response to the restraining energy.

The spectrum may be transmitted toward a sensor along an optical path. The restraining energy may be transmitted toward the body along at least a portion of the optical path. Optionally, the restrained body may move within the fluid by moving the restraining energy or the fluid. The restraining energy may sweep through the fluid to move the body toward a first site, at which the spectrum may optionally be sensed. The restraining energy may be swept through the fluid to move a second body toward a second site. The transmission of the restraining energy may be inhibited between the first and second sites so as to release the first body. Optionally, a series of bodies may be sequentially swept toward the first site for sequential sensing of their spectra.

In another aspect, the invention provides a multiplexed assay system comprising a support structure having an array of sites. A plurality of bodies each have a label for generating an identifiable spectrum in response to excitation energy. The bodies are restrainingly receivable at the sites. An optical train may image at least one site on a sensor surface. The optical train includes a wavelength dispersive element.

In yet another aspect, the invention provides a multiplexed assay system comprising a plurality of bodies released in a fluid. The bodies have labels for generating identifiable spectra. An energy transmitter is coupled to the fluid so as to spatially restrain at least one body with a restraining energy beam. A sensor is oriented to reserve the spectrum from the at least one body.

DESCRIPTION OF THE SPECIFIC EMBODIMENTS

The present invention generally provides improved devices, systems, methods, compositions of matter, kits, and the like for sensing and interpreting spectral information. The invention is particularly well-suited to take advantage of new compositions of matter which can generate signals at specific wavelengths in response to excitation energy. A particularly advantageous signal generation structure for use of the present invention is the semiconductor nanocrystal. Other useful signaling structures may also take advantage of the improvements provided by the present invention, including conventional fluorescent dies, radioactive and radiated elements and compounds, Raman scattering materials, and the like.

The invention can allow efficient sensing and/or identification of a large number of spectral codes, particularly when each code includes multiple signals. The invention may also enhance the reliability and accuracy with which such codes are read, and may thereby enable the use of large numbers of spectral codes within a relatively small region. Hence, the techniques of the present invention will find advantageous applications within highly multiplexed assays, inventory control in which a large number of small and/or fluid elements are intermingled, and the like.

Spectra Labeling

Figure 1:
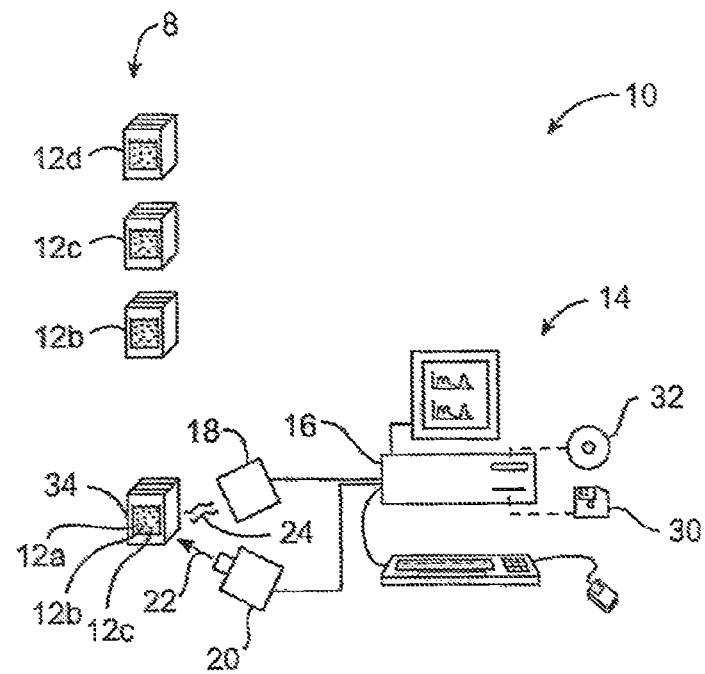
FIG. 1 schematically illustrates an imaging system and high-Throughput assay method according the principles of the present invention.

Referring now to FIG. 1, an inventory system 10 includes a library of labeled elements 12a, 12b, . . . (collectively referred to as elements 12) and an analyzer 14. Analyzer 14 generally includes a processor 16 coupled to a detector 18. An energy source 20 transmits an excitation energy 22 to a sensing field within a first labeled element 12a of library 8. In response to excitation energy 22, first labeled element 12a emits radiant energy 24 defining a spectral code. Spectral code of radiant energy 24 is sensed by detector 18 and the spectral code is interpreted by processor 16 so as to identify labeled element 12a.

Library 8 may optionally comprise a wide variety of elements. In many embodiments, labeled elements 12 may be separated. However, in the exemplary embodiment, the various labeled elements 12a, 12b, 12c, . . . are intermingled within a test fluid 34. A real imaging is facilitated by maintaining the labeled elements on or near a surface. As used therein, "areal imaging" means imaging of a two-dimensional area. Hence, fluid 34 may be contained in a thin, flat region between planar surfaces.

Preferably, detector 18 simultaneously images at least some of the signals generated by elements 12 from within a two-dimensional sensing field. In some embodiments, at least some of the spectral signals from within the sensing field are sequentially sensed using a scanning system. Regardless, maintaining each label as a spatially integral unit will often facilitate identification of the label. This discrete spatial integrity of each label is encompassed within the term "spatially resolved labels." Preferably, the spatial integrity of the beads and the space between beads will be sufficient to allow at least some of the beads to be individually resolved over all other beads, preferably allowing most of the beads to be individually resolved, and in many embodiments, allowing substantially all of the beads to be individually resolved.

The spectral coding of the present invention is particularly well-suited for identification of small or fluid elements which may be difficult to label using known techniques. Elements 12 may generally comprise a composition of matter, a biological structure, a fluid, a particle, an article of manufacture, a consumer product, a component for an assembly, or the like. All of these are encompassed within the term "identifiable substance."

The labels included with labeled elements 12 may be adhered to, applied to a surface of, and/or incorporated within the items of interest, optionally using techniques analogous to those of standard bar coding technologies. For example, spectral labeling compositions of matter (which emit the desired spectra) may be deposited on adhesive labels and applied to articles of manufacture. Alternatively, an adhesive polymer material incorporating the label might be applied to a surface of a small article, such as a jewel or a component of an electronic assembly. As the information in the spectral code does not depend upon the aerial surface of the label, such labels can be quite small.

In other embodiments, the library will comprise fluids (such as biological samples), powders, cells, and the like. While labeling of such samples using standard bar coding techniques can be quite problematic, particularly when a large number of samples are to be accurately identified, the spectral codes of the present invention can allow robust identification of a particular element from among ten or more library elements, a hundred or more library elements, a thousand or more library elements, and even ten thousand or more library elements.

The labels of the labeled elements 12 will often include compositions of matter which emit energy with a controllable wavelength/intensity spectrum. To facilitate identification of specific elements from among library 8, the labels of the elements may include combinations of differing compositions of matter to emit differing portions of the overall spectral code. In other embodiments, the signals may be defined by absorption (rather than emission) of energy, by Raman scattering, or the like. As used herein, the term "markers" encompasses compositions of matter which produce the different signals making up the overall spectra. A plurality of markers can be combined to form a label, with the signals from the markers together defining the spectra for the label.

The present invention generally utilizes one or more signals from one or more markers. The markers may comprise semiconductor nanocrystals, with the different markers often taking the form of different particle size distributions of semiconductor nanocrystals having different signal generation characteristics. One or more markers may be combined to form a spectral label which can generate an identifiable spectrum defining a spectral code, sometimes referred to as "spectral barcodes." These spectral codes can be used to track the location of a particular item of interest or to identify a particular item of interest.

In many spectral codes, the different signals will have varying signal characteristics which are used as elements of the code. For example, semiconductor nanocrystals used in the spectral coding scheme can be tuned to a desired wavelength to produce a characteristic spectral emission or signal by changing the composition and/or size of the semiconductor nanocrystal. Additionally, the intensity of the signal at a particular characteristic wavelength can also be varied (optionally by, at least in part, varying a number of semiconductor nanocrystals emitting or absorbing at a particular wavelength), thus enabling the use of binary or higher order encoding schemes. The information encoded by the semiconductor nanocrystals can be spectroscopically decoded from the characteristics of their signals, thus providing the location and/or identity of the particular item or component of interest. As used herein, wavelength and intensity are encompassed within the term "signal characteristics."

While spectral codes will often be described herein with reference to the signal characteristics of signals emitted with discrete, narrow peaks, it should be understood that semiconductor nanocrystals and other marker structures may generate signals having quite different properties. For example, signals may be generated by scattering, absorption, or the like, and alternative signal characteristics such as wavelength range width, slope, shift, or the like may be used in some spectral coding schemes.

Semiconductor Nanocrystals

Semiconductor nanocrystals are particularly well-suited for use as markers in a spectral code system because of their unique characteristics. Semiconductor nanocrystals have radii that are smaller than the bulk exciton Bohr radius and constitute a class of materials intermediate between molecular and bulk forms of matter. Quantum confinement of both the electron and hole in all three dimensions leads to an increase in the effective band gap of the material with decreasing crystallite size. Consequently, both the optical absorption and emission of semiconductor nanocrystals shift to the blue (higher energies) with decreasing size. Upon exposure to a primary light source, each semiconductor nanocrystal distribution is capable of emitting energy in narrow spectral linewidths, as narrow as 20 30 nm, and with a symmetric, nearly Gaussian line shape, thus providing an easy way to identify a particular semiconductor nanocrystal. The linewidths are dependent on the size heterogeneity, i.e., monodispersity, of the semiconductor nanocrystals in each preparation. Single semiconductor nanocrystal complexes have been observed to have full width at half max (FWHM) as narrow as 12 15 nm. In addition semiconductor nanocrystal distributions with larger linewidths in the range of 40 60 nm can be readily made and have the same physical characteristics as semiconductor nanocrystals with narrower linewidths.

Exemplary materials for use as semiconductor nanocrystals in the present invention include, but are not limited to group II VI, III V, and group IV semiconductors such as ZnS, ZnSe, ZnTe, CdS, CdSe, CdTe, GaN, GaP, GaAs, GaSb, InP, InAs, InSb, AlS, AlP, AlSb, PbS, PbSe, Ge, Si, and ternary and quaternary mixtures or alloys thereof. The semiconductor nanocrystals are characterized by their nanometer size. By "nanometer" size, it is meant less than about 150 Angstroms (A), and preferably in the range of 12 150 A.

The selection of the composition of the semiconductor nanocrystal, as well as the size of the semiconductor nanocrystal, affects the signal characteristics of the semiconductor nanocrystal. Thus, a particular composition of a semiconductor nanocrystal as listed above will be selected based upon the spectral region being monitored. For example, semiconductor nanocrystals that emit energy in the visible range include, but are not limited to, CdS, CdSe, CdTe, and ZnTe. Semiconductor nanocrystals that emit energy in the near IR range include, but are not limited to, InP, InAs, InSb, PbS, and PbSe. Finally, semiconductor nanocrystals that emit energy in the blue to near-ultraviolet include, but are not limited to, ZnS and GaN. For any particular composition selected for the semiconductor nanocrystals to be used in the inventive system, it is possible to tune the emission to a desired wavelength within a particular spectral range by controlling the size of the particular composition of the semiconductor nanocrystal.

In addition to the ability to tune the signal characteristics by controlling the size of a particular semiconductor nanocrystal, the intensities of that particular emission observed at a specific wavelength are also capable of being varied, thus increasing the potential information density provided by the semiconductor nanocrystal coding system. In some embodiments, 2 15 different intensities may be achieved for a particular emission at a desired wavelength, however, more than fifteen different intensities may be achieved, depending upon the particular application of the inventive identification units. For the purposes of the present invention, different intensities may be achieved by varying the concentrations of the particular size semiconductor nanocrystal attached to, embedded within or associated with an item or component of interest, by varying a Quantum yield of the nanocrystals, by varyingly quenching the signals from the semiconductor nanocrystals, or the like. Nonetheless, the spectral coding schemes may actually benefit from a simple binary structure, in which a given wavelength is either present our absent, as described below.

In a particularly preferred embodiment, the surface of the semiconductor nanocrystal is also modified to enhance the efficiency of the emissions, by adding an overcoating layer to the semiconductor nanocrystal. The overcoating layer is particularly preferred because at the surface of the semiconductor nanocrystal, surface defects can result in traps for electron or holes that degrade the electrical and optical properties of the semiconductor nanocrystal. An insulting layer (having a bandpass layer typically with a bandgap energy greater than the core and centered thereover) at the surface of the semiconductor nanocrystal provides an atomically abrupt jump in the chemical potential at the interface that eliminates energy states that can serve as traps for the electrons and holes. This results in higher efficiency in the luminescent process.

Suitable materials for the overcoating layer include semiconductors having a higher band gap energy than the semiconductor nanocrystal. In addition to having a band gap energy greater than the semiconductor nanocrystals, suitable materials for the overcoating layer should have good conduction and valence band offset with respect to the semiconductor nanocrystal. Thus, the conduction band is desirably higher and the valence band is desirably lower than those of the semiconductor nanocrystal. For semiconductor nanocrystals that emit energy in the visible (e.g., CdS, CdSe, CdTe, ZnSe, ZnTe, GaP, GaAs) or near IR (e.g., InP, InAs, InSb, PbS, PbSe), a material that has a band gap energy in the ultraviolet regions may be used. Exemplary materials include ZnS, GaN, and magnesium chalcogenides, (e.g., MgS, MgSe, and MgTe). For semiconductor nanocrystals that emit in the near IR, materials having a band gap energy in the visible, such as CdS, or CdSe, may also be used. While the overcoating will often have a higher bandgap than the emission energy, the energies can be, for example, both within the visible range. The overcoating layer may include as many as 8 monolayers of the semiconductor material. The preparation of a coated semiconductor nanocrystal may be found in U.S. patent application Ser. No. 08/969,302 filed Nov. 13, 1997, entitled "Highly Luminescent Color-Selective Materials"; Dabbousi et al., J. Phys. Chem B., Vol. 101, 1997, pp. 9463; and Kuno et al., J. Phys. Chem., Vol. 106, 1997, pp. 9869. Fabrication and combination of the differing populations of semiconductor nanocrystals may be further understood with reference to U.S. patent application Ser. No. 09/397,432, previously incorporated herein by reference.

It is often advantageous to combine different markers of a label into one or more labeled body. Such labeled bodies may help spatially resolve different labels from intermingled items of interest, which can be beneficial during identification. These label bodies may comprise a composition of matter including a polymeric matrix and a plurality of semiconductor nanocrystals, which can be used to encode discrete and different absorption and emission spectra. These spectra can be read using a light source to cause the label bodies to absorb or emit light. By detecting the light absorbed and/or emitted, a unique spectral code may be identified for the labels. In some embodiments, the labeled bodies may further include markers beyond the label bodies. These labeled bodies will often be referred to as "beads" herein, and beads which have assay capabilities may be called "probes." The structure and use of such probes, including their assay capabilities, are more fully described in U.S. patent application Ser. No. 09/259,982, previously incorporated by reference.

Fabrication of Labeled Beads

Figure 2:
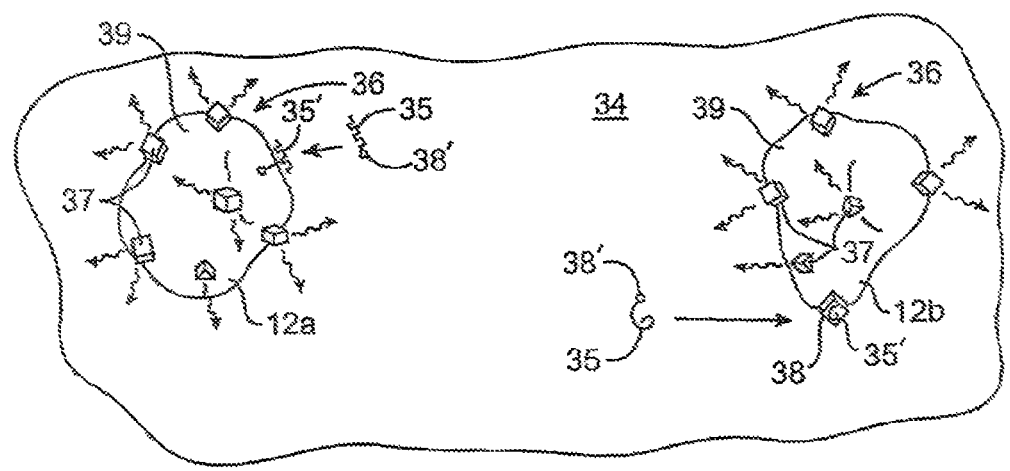
FIG. 2 schematically illustrates probes having spectral labels and assay markers, in which the probes comprise bead structures disposed within a test fluid.

Referring now to FIG. 2, first and second labeled elements 12a, 12b within test fluid 34 are formed as separate semiconductor nanocrystal probes. Each probe includes a label 36 formed from one or more populations of substantially monodisperse semiconductor nanocrystals 37. The individual populations of semiconductor nanocrystals will often be mono-disperse so as to provide a sufficient signal intensity at a uniform wavelength for convenient sensing of the various signals within the code. The exemplary probes further include assay markers 38, together with a probe matrix or body material 39, which acts as a binding agent to keep the various markers together in a structural unit. Assay markers 38 generate signals indicating results of an assay, and are schematically illustrated as semiconductor nanocrystals having at least one moiety with selective affinity for an associated test substance 35 which may be present within sample fluid 34. Preparation of the spectrally encoded probes will now be described, followed by a brief description of the use and structure of assay markers 38.

A process for encoding spectra codes into label body materials using a feedback system can be based on the absorbance and luminescence of the semiconductor nanocrystals in a solution that can be used to dye the materials. More specifically, this solution can be used for encoding of a plurality of semiconductor nanocrystals into a material when that material is a polymeric bead.

A variety of different materials can be used to prepare these compositions. In particular, polymeric bead materials are an appropriate format for efficient multiplexing and demultiplexing of finite-sized materials. These label body beads can be prepared from a variety of different polymers, including but not limited to polystyrene, cross-linked polystyrene, polyacrylic, polysiloxanes, polymeric silica, latexes, dextran polymers, epoxies, and the like. The materials have a variety of different properties with regard to swelling and porosity, which are well understood in the art. Preferably, the beads are in the size range of approximately 10 nm to 1 mm, more preferably in a size range of approximately 100 nm to 0.1 mm, often being in a range from 50 nm to 1,000,000 nm, and can be manipulated using normal solution techniques when suspended in a solution.

Discrete emission spectra can be encoded into these materials by varying the amounts and ratios of different semiconductor nanocrystals, either the size distribution of semiconductor nanocrystals, the composition of the semiconductor nanocrystals, or other property of the semiconductor nanocrystals that yields a distinguishable emission spectrum, which are embedded into, attached to or otherwise associated with the material. The semiconductor nanocrystals of the invention can be associated with the material by adsorption, absorption, covalent attachment, by co-polymerization or the like. The semiconductor nanocrystals have absorption and emission spectra that depend on their size and composition. These semiconductor nanocrystals can be prepared as described in Murray et. al., (1993) J. Am. Chem. Soc. 115:8706 8715; Guzelian et. al., (1996) J. Phys. Chem. 100; 7212 7219; or International Publication No. WO 99/26299 (inventors Bawendi et al.). The semiconductor nanocrystals can be made further luminescent through overcoating procedures as described in Danek et. al., (1966) Chem. Mat. 8(1):173 180; Hines et. al., (1996) J. Phys. Chem. 100:468 471; Peng et. al., (1997) J. Am. Chem. Soc. 119:7019 7029; or Daboussi et. al., (1997) J. Phys. Chem.-B, 101:9463 9475.

The desired spectral emission properties may be obtained by mixing semiconductor nanocrystals of different sizes and/or compositions in a fixed amount and ratio to obtain the desired spectrum. The spectral emission of this staining solution can be determined prior to treatment of the material therewith. Subsequent treatment of the material (through covalent attachment, co-polymerization, passive absorption, swelling and contraction, or the like) with the staining solution results in a material having the designed spectral emission property. These spectra may be different under different excitation sources. Accordingly, it is preferred that the light source used for the encoding procedure be as similar as possible (preferably of the same wavelength and/or intensity) to the light source that will be used for the decoding. The light source may be related in a quantitative manner, so that the emission spectrum of the final material may be deduced from the spectrum of the staining solution.

A number of semiconductor nanocrystal solutions can be prepared, each having a distinct distribution of sizes and compositions, and consequently a distinct emission spectrum, to achieve a desired emission spectrum. These solutions may be mixed in fixed proportions to arrive at a spectrum having the predetermined ratios and intensities of emission from the distinct semiconductor nanocrystals suspended in that solution. Upon exposure of this solution to a light source, the emission spectrum can be measured by techniques that are well established in the art. If the spectrum is not the desired spectrum, then more of a selected semiconductor nanocrystal solution can be added to achieve the desired spectrum and the solution titrated to have the correct emission spectrum. These solutions may be colloidal solutions of semiconductor nanocrystals dispersed in a solvent, or they may be pre-polymeric colloidal solutions, which can be polymerized to form a matrix with semiconductor nanocrystals contained within. While ratios of the quantities of constituent solutions and the final spectrum intensities need not be the same, it will often be possible to derive the final spectra from the quantities (and/or the quantities from the desired spectra.)

The solution luminescence will often be adjusted to have the desired intensities and ratios under the exact excitation source that will be used for the decoding. The spectrum may also be prepared to have an intensity and ratio among the various wavelengths that are known to produce materials having the desired spectrum under a particular excitation source. A multichannel auto-pipettor connected to a feedback circuit can be used to prepare a semiconductor nanocrystal solution having the desired spectral characteristics, as described above. If the several channels of the titrator/pipettor are charged or loaded with several unique solutions of semiconductor nanocrystals, each having a unique excitation and emission spectrum, then these can be combined stepwise through addition of the stock solutions. In between additions, the spectrum may be obtained by exposing the solution to a light source capable of causing the semiconductor nanocrystals to emit, preferably the same light source that will be used to decode the spectra of the encoded materials. The spectrum obtained from such intermediate measurements may be judged by a computer based on the desired spectrum. If the solution luminescence is lacking in one particular semiconductor nanocrystal emission spectrum, stock solution containing that semiconductor nanocrystal may be added in sufficient amount to bring the emission spectrum to the desired level. This procedure can be carried out for all different semiconductor nanocrystals simultaneously, or it may be carried out sequentially.

Once the staining solution has been prepared, it can be used to incorporate a unique luminescence spectrum into the materials of this invention. If the method of incorporation of the semiconductor nanocrystals into the materials is absorption or adsorption, then the solvent that is used for the staining solution may be one that is suitable for swelling the materials. Such solvents are commonly from the group of solvents including dichloromethane, chloroform, dimethylformamide, tetrahydrofuran and the like. These can be mixed with a more polar solvent, for example methanol or ethanol, to control the degree and rate of incorporation of the staining solution into the material. When the material is added to the staining solution, the material will swell, thereby causing the material to incorporate a plurality of semiconductor nanocrystals in the relative proportions that are present in the staining solution. In some embodiments, the semiconductor nanocrystals may be incorporated in a different but predictable proportion. When a more polar solvent is added, after removal of the staining solution from the material, material shrinks, or unswells, thereby trapping the semiconductor nanocrystals in the material. Alternatively, semiconductor nanocrystals can be trapped by evaporation of the swelling solvent from the material. After rinsing with a solvent in which the semiconductor nanocrystals are soluble, yet that does not swell the material, the semiconductor nanocrystals are trapped in the material, and may not be rinsed out through the use of a non-swelling, non-polar solvent. Such a non-swelling, non-polar solvent is typically hexane or toluene. The materials can be separated and then exposed to a variety of solvents without a change in the emission spectrum under the light source. When the material used is a polymer bead, the material can be separated from the rinsing solvent by centrifugation or evaporation or both, and can be redispersed into aqueous solvents and buffers through the use of detergents in the suspending buffer, as is well known in the art.

The above procedure can be carried out in sequential steps as well. A first staining solution can be used to stain the materials with one population of semiconductor nanocrystals. A second population of semiconductor nanocrystals can be prepared in a second staining solution, and the material exposed to this second staining solution to associate the semiconductor nanocrystals of the second population with the material. These steps can be repeated until the desired spectral properties are obtained from the material when excited by a light source, optionally using feedback from measurements of the interim spectra generated by the partially stained bead material to adjust the process.

The semiconductor nanocrystals can be attached to the material by covalent attachment, and/or by entrapment in pores of the swelled beads. For instance, semiconductor nanocrystals are prepared by a number of techniques that result in reactive groups on the surface of the semiconductor nanocrystal. See, e.g., Bruchez et. al., (1998) Science 281: 2013 2016; and Ghan et. al., (1998) Science 281:2016 2018, Golvin et. al., (1992) J. Am. Chem. Soc. 114:5221 5230; Katari et. al. (1994) J, Phys. Chem. 98:4109 4117; Steigerwald et, al. (1987) J. Am. Chem. Soc. 110:3046. The reactive groups present on the surface of the semiconductor nanocrystals can be coupled to reactive groups present on the surface of the material. For instance, semiconductor nanocrystals which have carboxylate groups present on their surface can be coupled to beads with amine groups using a carbo-diimide activation step, or a variety of other methods well known in the art of attaching molecules and biological substances to bead surfaces. In this case, the relative amounts of the different semiconductor nanocrystals can be used to control the relative intensities, while the absolute intensities can be controlled by adjusting the reaction time to control the number of reacted sites in total. After the bead materials are stained with the semiconductor nanocrystals, the materials are optionally rinsed to wash away unreacted semiconductor nanocrystals.

Referring once again to FIG. 2, labeled elements 12a, 12b (here in the form of semiconductor nanocrystal probes) may be useful in assays in a wide variety of forms. Utility of the probes for assays benefits significantly from the use of moieties or affinity molecules 35', as schematically illustrated in FIG. 2, which may optionally be supported directly by label marker 37 of label 36, by the probe body matrix 39, or the like. Moieties 35' can have selective affinity for an associated detectable substance 35, as schematically illustrated by correspondence of symbol shapes in FIG. 2. The probes may, but need not necessarily, also include an integrated assay marker 38. In some embodiments, the assay marker will instead be coupled to the probes by coupling of detectable substance 35 to moiety 35'. In other words, the assay marker 38' may (at least initially) be coupled to the detectable substance 35, typically by binding of a dye molecule, incorporation of a radioactive isotope, or the like. The assay markers may thus be coupled to the probe by the interaction between the moieties 35' and the test or detectable substances 35. In other assays, the assay results may be determined by the presence or absence of the probe or bead (for example, by washing away probes having an unattached moiety) so that no dedicated assay marker need be provided.

In alternative embodiments, the material used to make the codes does not need to be semiconductor nanocrystals. For example, any fluorescent material or combination of fluorescent materials that can be finely tuned throughout a spectral range and can be excited optically or by other means might be used. For organic dyes, this may be possible using a number of different dyes that are each spectrally distinct.

This bead preparation method can be used generically to identify identifiable substances, including cells and other biological matter, objects, and the like. Pre-made mixtures of semiconductor nanocrystals, as described above, are attached to objects to render them subsequently identifiable. Many identical or similar objects can be coded simultaneously, for example, by attaching the same semiconductor nanocrystal mixture to a batch of microspheres using a variety of chemistries known in the art. Alternatively, codes may be attached to objects individually, depending on the objects being coded. In this case, the codes do not have to be pre-mixed and may be mixed during application of the code, for example using an inkjet printing system to deliver each species of semiconductor nanocrystals to the object. The use of semiconductor nanocrystal probes in chemical and/or biological assays is more fully described in U.S. patent application Ser. No. 09/259,982 filed Mar. 1, 1999, the full disclosure of which is incorporated herein by reference.

The semiconductor nanocrystal probes of FIG. 2 may also be utilized to detect the occurrence of an event. This event, for example, may cause the source from which energy is transferred to assay marker 38 to be located spatially proximal to the semiconductor nanocrystal probe. Hence, the excitation energy from energy source 20 may be transferred either directly to assay markers 38, 38', or indirectly via excitation of one or more energy sources adjacent the semiconductor nanocrystal probes due to bonding of the test substances 35 to the moiety 35'. For example, a laser beam may be used to excite a proximal source such as a semiconductor nanocrystal probe 38' attached to one of the test substances 35 (to which the affinity molecule selectively attaches), and the energy emitted by this semiconductor nanocrystal 38' may then excite an assay marker 38 affixed to the probe matrix.

Reading Beads

Referring once again to FIG. 1, energy source 20 generally directs excitation energy 22 in such a form as to induce emission of the spectral code from labeled element 12a. In one embodiment, energy source 20 comprises a source of light, the light preferably having a wavelength shorter than that of the spectral code. Energy source 20 may comprise a source of blue or ultraviolet light, optionally comprising a broad band ultraviolet light source such a deuterium lamp, optionally with a filter. Energy source 20 may comprise an Xe or Hg UV lamp, or a white light source such as a xenon lamp or a deuterium lamp, preferably with a short pass or bandpass UV filter disposed along the excitation energy path from the lamp to the labeled element 12 so as to limit the excitation energy to the desired wavelengths. Still further alternative excitation energy sources include any of a number of continuous wave (cw) gas lasers, including (but not limited to) any of the argon ion laser lines (457 nm, 488 nm, 514 nm, etc.), a HeCd laser, a solid-state diode laser (preferably having a blue or ultraviolet output such as a GaN based laser, a GaAs based laser with frequency doubling, a frequency doubled or tripled output of a YAG or YLF based laser, or the like), any of the pulsed lasers with an output in the blue or ultraviolet ranges, light emitting diodes, or the like.

The excitation energy 22 from energy source 20 will induce labeled element 12a to emit identifiable energy 24 having the spectral code, with the spectral code preferably comprising signals having relatively narrow peaks so as to define a series of distinguishable peak wavelengths and associated intensities. The peaks will typically have a half width of about 100 nm or less, preferably of 70 nm or less, more preferably 50 nm or less, and ideally 30 nm or less. In many embodiments, a plurality of separate signals will be included in the spectral code as sensed by sensor 18. As semiconductor nanocrystals are particularly well-suited for generating luminescent signals, identifiable energy 24 from label 12a will often comprise light energy. To help interpret the spectral code from the identifiable energy 24, the light energy may pass through one or more monochromator. A Charge-Coupled Device (CCD) camera or some other two-dimensional detector of sensor 18 can sense and/or record the images for later analysis. In other embodiments, a scanning system may be employed, in which the labeled element to be identified is scanned with respect to a microscope objective, with the luminescence put through a single monochromator or a grating or prism to spectrally resolve the colors. The detector can be a diode array that records the colors that are emitted at a particular spatial position, a two-dimensional CCD, or the like.

Figure 1A:
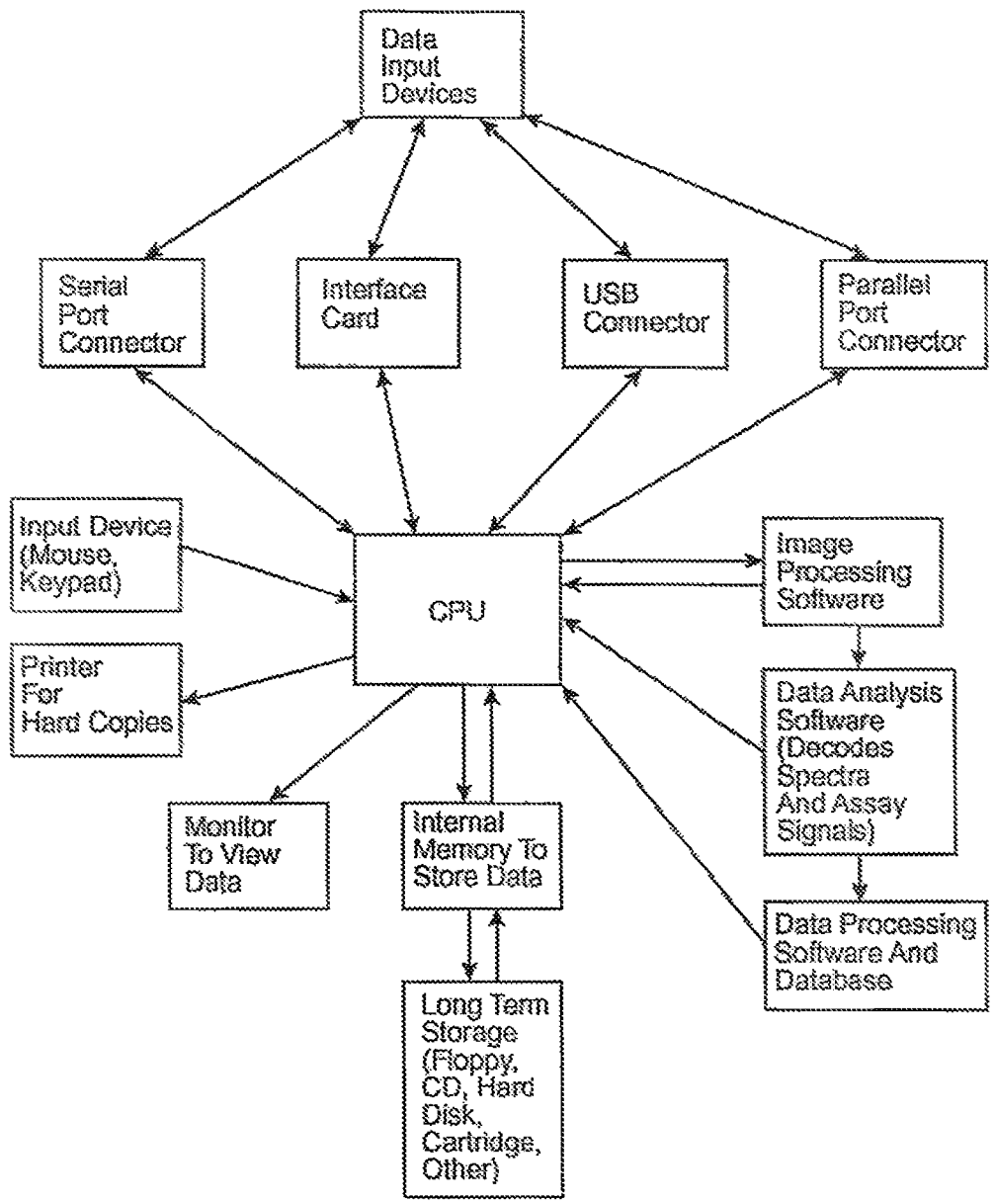
FIG. 1A schematically illustrates an exemplary processor for the system of FIG. 1.

Information regarding these spectra from the labeled elements 12 will generally be transmitted as signals sent from sensor 18 to processor 16, the processor typically comprising a general purpose computer. Processor 16 will typically include a central processing unit, ideally having a processing capability at least equivalent to a Pentium I® processor, although simpler systems might use processing capabilities equivalent to a Palm® handheld processor or more. Processor 16 will generally have input and output capabilities and associated peripheral components, including an output device such as a monitor, an input such as a keyboard, mouse, and/or the like, and will often have a networking connection such as an Ethernet, an Intranet, an Internet, and/or the like. An exemplary processing block diagram is schematically illustrated in FIG. 1A.

Processor 16 will often make use of a tangible media 30 having a machine-readable code embodying method steps according to one or more methods of the present invention. A database 32, similarly embodied in a machine-readable code, will often include a listing of the elements included in library 8, the spectral codes of the labels associated with the elements, and a correlation between specific library elements and their associated codes. Processor 16 uses the information from database 32 together with the spectrum characteristics sensed by sensor 18 to identify a particular library element 12a. The machine-readable code of program instructions 30 and database 32 may take a wide variety of forms, including floppy disks, optical discs (such as CDs, DVDs, rewritable CDs, and the like), alternative magnetic recording media (such as tapes, hard drives, and the like), volatile and/or nonvolatile memories, software, hardware, firmware, or the like.

As illustrated in FIG. 1, methods for detecting and classifying spectral labels (such as encoded materials and beads) may comprise exposing the labels to light of an excitation source so that the semiconductor nanocrystals of the label are sufficiently excited to emit light. This excitation source is preferably of an energy capable of exciting the semiconductor nanocrystals to emit light and may be of higher energy (and hence, shorter wavelength) than the shortest emission wavelength of the semiconductor nanocrystals in the label. Alternatively the excitation source can emit light of longer wavelength if it is capable of exciting some of the semiconductor nanocrystals disposed in the matrix to emit light, such as using two-photon excitation. This excitation source is preferably chosen to excite a sufficient number of different populations of semiconductor nanocrystals to allow unique identification of the encoded materials. For example, using materials stained in a 1:2 ratio of red to blue and a 1:3 ratio of red to blue, it may not be sufficient to only excite the red emitting semiconductor nanocrystals, (e.g., by using green or yellow light, of the sample in order to resolve these beads). It would be desirable to use a light source with components that are capable of exciting the blue emitting and the red emitting semiconductor nanocrystals simultaneously, (e.g., violet or ultraviolet). There may be one or more light sources used to excite the populations of the different semiconductor nanocrystals simultaneously or sequentially, but each light source may selectively excite sub-populations of semiconductor nanocrystals that emit at lower energy than the light source (to a greater degree than higher energy emitting sub-populations), due to the absorbance spectra of the semiconductor nanocrystals. Ideally, a single excitation energy source will be sufficient to induce the labels to emit identifiable spectra.

Spectral Codes

Figure 2A:
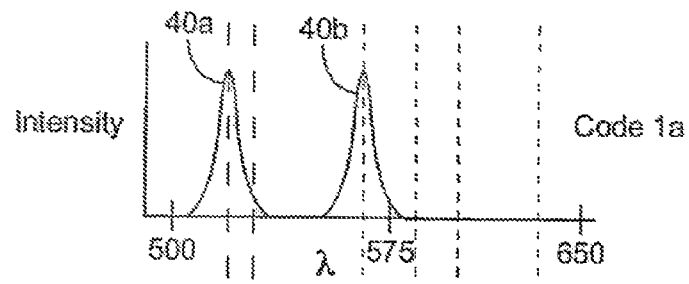
FIGS. 2A-2E schematically illustrate spectral codes or labels having a plurality of signals.
Figure 2B:
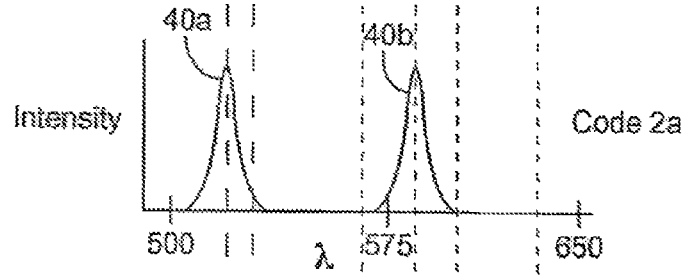
Figure 2C:
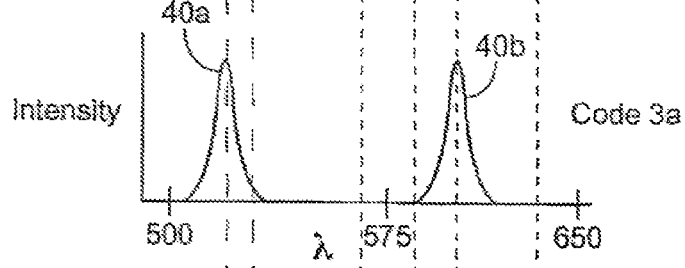
Figure 2D:
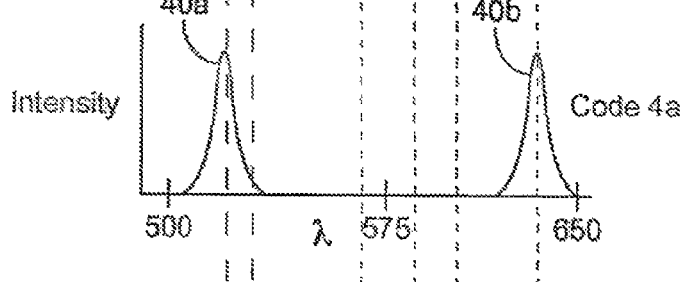
Figure 2E:
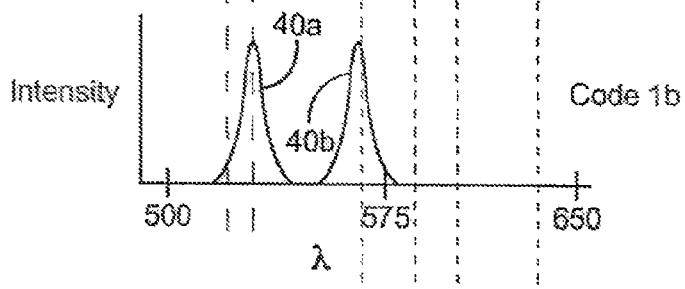

Referring now to FIGS. 2A 2E, the use of a plurality of different signals within a single spectral label can be understood. In this simple example, a coding system is shown having two signals. A first signal has a wavelength peak 40a at a first discreet wavelength, while a separate signal has a different wavelength peak 40b. As shown in FIGS. 2A 2D, varying peak 40b while the first peak 40a remains at a fixed location defines a first family of spectral codes 1a through 4a. Moving the first peak 40a to a new location allows a second family of spectral codes to be produced, as can be understood with reference to FIG. 2E.

The simple code system illustrated in FIGS. 2A 2E includes only two signals, but still allows a large number of identifiable spectra. More complex spectral codes having larger numbers of peaks can significantly increase the number of codes. Additionally, the intensities of one or more of the peaks may also be varied, thereby providing still higher order codes having larger numbers of separately identifiable members.

Spectra Code Reading Systems

In general, fluorescent labeling is a powerful technique for tracking components in biological systems. For instance, labeling a portion of a cell with a fluorescent marker can allow one to monitor the movement of that component within the cell. Similarly, labeling an analyte in a bioassay can allow one to determine its presence or absence, even at vanishingly small concentrations. The use of multiple fluorophores with different emission wavelengths allows different components to be monitored simultaneously. Applications such as spectral encoding can take full advantage of multicolor fluorophores, potentially allowing the simultaneous detection of millions of analytes.

When imaging samples labeled with multiple chromophores, it is desirable to resolve spectrally the fluorescence from each discrete region within the sample. As an example, an assay may be prepared in which polymer beads have been labeled with two different chromophores and the results of the assay may be determined by the ratio of the two types of beads within the final sample. One could imagine immobilizing the beads and counting each of the colors. Electronic imaging may involve a technique for acquiring an image of the sample in which spectral information is available at each discrete point. While the human eye is exceptionally good at distinguishing colors, typical electronic photodetectors are often effectively color-blind. As such, additional optical components are often used in order to acquire spectral information.

Many techniques might be combined with the present invention. Fourier transform spectral imaging (Malik et al. (1996) J. Microsc. 182:133; Brenan et al. (1994) Appl. Opt 33:7520) and Hadamard transform spectral imaging (Treado et al. (1989) Anal. Chem 61:732A; Treado et al. (1990) Appl. Spectrosc. 44:1 4; Treado et al. (1990) Appl. Spectrosc. 44:1270; Hammaker et al. (1995) J. Mol. Struct. 348:135; Mei et al. (1996) J. Anal. Chem. 354:250; Flateley et al. (1993) Appl. Spectrosc. 47:1464); imaging through variable interference (Youvan (1994) Nature 369:79: Goldman et al. (1992) Biotechnology 10:1557); acousto-optical (Mortensen et al. (1996) IEEE Trans. Inst. Meas. 45:394; Turner et al (1996) Appl. Spectrosc. 50:277); liquid crystal filters (Morris et al. (1994) Appl. Spectrosc. 48:857); or simply scanning a slit or point across the sample surface (Colarusso et al. (1998) Appl. Spectrosc. 52: 106A) are methods capable of generating spectral and spatial information across a two-dimensional region of a sample.

Figure 3:
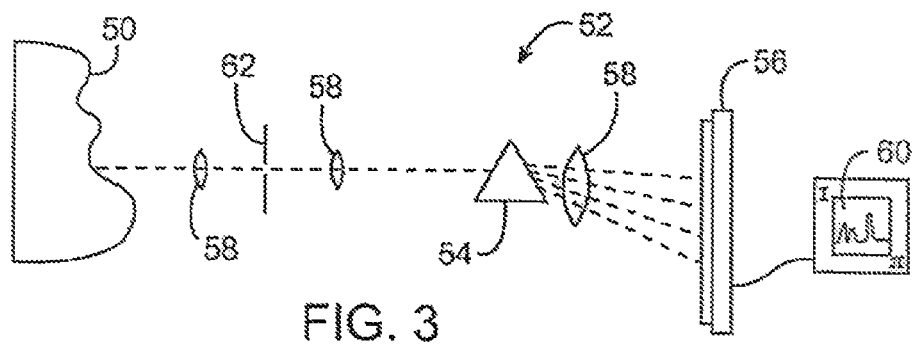
FIG. 3 schematically illustrates a system and method for determining a spectrum from a relatively large object by use of an aperture.

Referring now to FIG. 3, a system and method for reading spectral information from an arbitrarily large object 50 generally makes use of a detector 52 including a wavelength dispersive element 54 and a sensor 56. Imaging optics 58 image object 50 onto a surface of sensor 56. Wavelength dispersive element 54 spectrally disperses the image across the surface of the sensor, distributing the image based on the wavelengths of the image spectra.

As object 50 is relatively large when imaged upon sensor 56, differentiation of the discreet wavelengths within a spectrum 60 is facilitated by the use of an aperture 62. As aperture 62 allows only a small region of the image through wavelength dispersive element 54, the wavelength dispersive element separates the image components based on wavelength alone (rather than on a combination of wavelength and position along the surface of image 50). Spectra 60 may then be directly determined based on the position of the diffracted image upon sensor 56, together with the intensity of image wavelength components as measured by the sensor.

Figure 4:
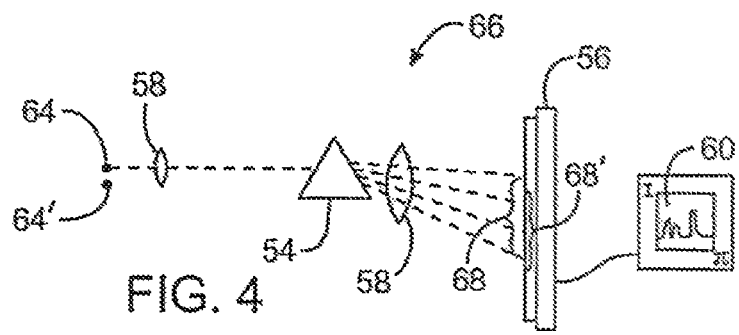
FIG. 4 schematically illustrates a method and structure for determining a spectrum from a small object, such as an assay probe having semiconductor nanocrystal markers, without using an aperture.

Referring now to FIG. 4, a spectra 60 of a spectrally labeled nanocrystal bead 64 may be performed using a detector 66 without an aperture. As bead 64 has a signal generating area (as imaged by imaging optics 58) which is much smaller than a sensing surface of sensor 56, bead 64 can act as a point-source of spectra 60. The various signals of the spectral code emanate from the small surface area of the bead, so that the signal distribution across the sensor surface is dominated by the wavelength dispersion, and no limiting of the image via an aperture is required. As used herein, a "true point source" is a light source with a dimension which is at least as small as a minimum, diffraction limited determinable dimension. A light source which is larger than a true point source may "act" or be "used," "treated," or "analyzed" (or the like) as a point source if it has a dimension or size which is sufficiently small that its size acts like an aperture.

As described above, it will often be advantageous to include a plurality of different spectrally labeled beads within a fluid. These labeled beads will often be supported by the surrounding fluid, and/or will be movable with the fluid, particularly in high-throughput multiplexed bead-based assays. Optionally, the beads may have a size sufficient to define a suspension within the surrounding test fluid. In some embodiments, the beads may comprise a colloid within the test fluid. In some embodiments, beads 64 may be movably supported by a surface of a vessel containing the test fluid, for example, being disposed on the bottom surface of the vessel (where probe 64 has a density greater than that of the test fluid). In other embodiments, the beads may be affixed to a support structure and/or to each other. Still further alternatives are possible, such as for probe 64 to be floating on an upper surface of the test fluid, for the bead or beads to be affixed to or disposed between cooperating surfaces of the vessel to maintain the positioning of the bead or beads, for the bead or beads to be disposed at the interface between two fluids, and the like.

Figure 5A:
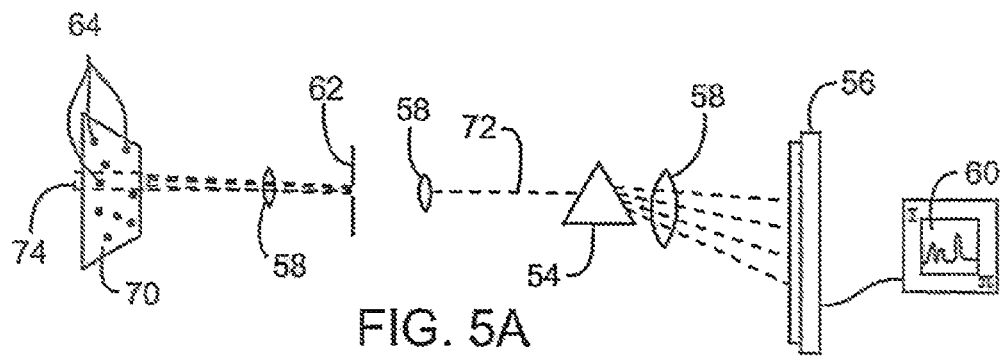
FIGS. 5A and 5B schematically illustrate a system and method for determining absolute spectra from a plurality of semiconductor nanocrystals by limiting the viewing field with an aperture and by spectrally dispersing the apertured image.

As was described above, it will often be advantageous to include numerous beads 64 within a single test fluid so as to perform a plurality of assays. Similarly, it will often be advantageous to identify a large number of fluids or small discreet elements within a single viewing area without separating out each spectral label from the combined labeled elements. As illustrated in FIG. 4, the dispersed spectral image 68 of bead 64 upon sensor 56 will depend on both the relative spectra generated by the bead, and on the position of the bead. For example, bead 64' is imaged onto a different portion 68' of sensor 56, which could lead to misinterpretation of the wavelengths of the spectra if the location of bead 64' is not known. So long as an individual bead 64 can be accurately aligned with the imaging optics 58 and sensor system 66, absolute spectral information can be obtained. However, as can be understood with reference to FIG. 5A, a plurality of beads 64 will often be distributed throughout an area 70.

Figure 5B:
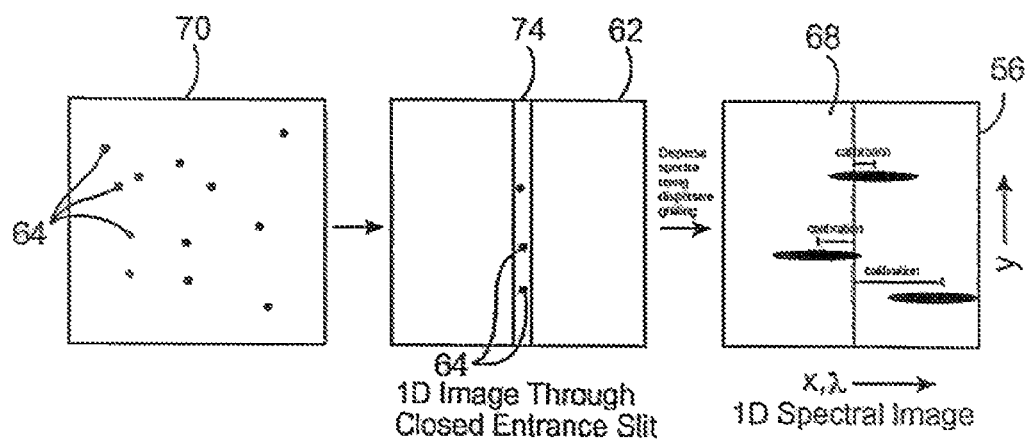

To ensure that only beads 64 which are aligned along an optical axis 72 are imaged onto sensor 56, aperture 62 restricts a sensing field 74 of the sensing system. Where sensor 56 comprises an areal sensor such a charge couple device (COD), aperture 62 may comprise a slit aperture so that spectral wavelengths .lamda. can be determined from the position of the dispersed images 68 along a dispersion axis of wavelength dispersive element 54 for multiple beads 64 distributed along the slit viewing field 74 along a second axis y, as can be understood with reference to FIG. 5B. Absolute accuracy of the spectral readings will vary inversely with a width of aperture slit 62, and the number of readings (and hence total reading time) for reading all the beads in area 70 will be longer as the slit gets narrower. Nonetheless, the beads 64 within the two-dimensional area 70 may eventually be read by the system of FIGS. 5A and 5B with a scanning system which moves the slit relative to beads 64 (using any of a variety of scanning mechanisms, such as movable mirrors, a movable aperture, a flow of the beads passed a fixed aperture, or the like).

Sequential sensing of the spectra may be performed by moving the aperture relative to the sensing field, by software, by moving the beads (or other signal sources) relative to the optical train or scanning system, or even by scanning one of an excitation energy or the beads relative to the other. Aperture scanning may be effected by a galvanometer, by a liquid crystal display (LCD) selective transmission arrangement, by other digital arrays, or by a digital micro-mirror array (DMD). Bead scanning systems may also use a fluid flow past a slit aperture, with the beads flowing with the fluid. Such bead flow systems result in movement of the aperture relative to the beads, even when the aperture remains fixed, as movement may be determined relative to the bead's frame of reference.

Figure 5C:
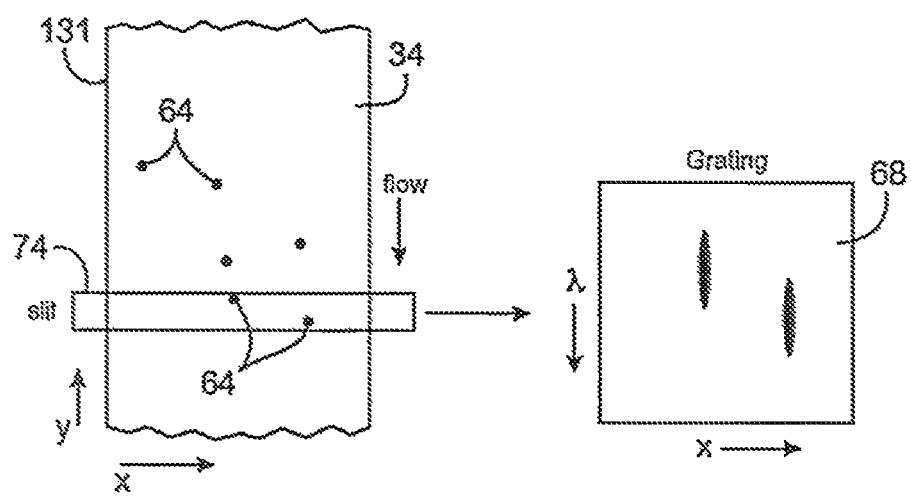
FIG. 5C schematically illustrates a fluid flow assay scanning system and method.

Referring now to FIG. 5C, a simple fluid-flow assay system can make use of many of the structures and methods described herein above. In the illustrated embodiment, a test fluid 34 flows through a channel 131 so that beads 64 move across sensing field 74. Beads 64 within the slit-apertured sensing region are spectrally dispersed and imaged as described above. As the location of the slit-aperture is known, absolute spectral information regarding the label spectra and assay signals may be determined from dispersed image 68. When a plurality of beads are within sensing region 74 but separated along the x axis as shown, multiple beads may be read simultaneously by a CCD, or the like. Flowing of the beads sequentially through sensing region 74 may allow simultaneous assay preparation and reading using flow injection analysis techniques, or the like.

Imaging of sensing region 74 may be facilitated by providing a thin, flat channel 131 so that beads 64 are near opposed major surfaces of the channel, with at least one of the channel surfaces being defined by a material which is transparent to the spectra and marker signals. This fluid-flow system may be combined with many aspects of the systems described hereinabove, for example, by providing two different energy sources for the label spectra and assay markers, by areal imaging of beads 64 distributed throughout a two-dimensional sensing region adjacent to or overlapping with slit-apertured sensing region 74, and the like.

Restrained Position Beads

Techniques to analyze bead-based assays can be flow based and/or imaging based. In the flow-based analysis, an instrument such as sheath flow cytometer is used to read the fluorescence and scatter information from each bead individually. Flow methods can have the disadvantage of requiring a relatively large volume of sample to fill dead volume in the lines and may complicate averaging or re-analysis of data points. Flow methods allow a large number of beads to be analyzed from a given sample. Imaging based systems, such as the Biometric Image™ system, scan a surface to find fluorescence signals. Advantages over the flow system may include small (<20 microliter) sample volumes and the ability to average data to improve signal to noise. A potential disadvantage is the use of a large area in order to keep beads separated, and the dependence on beads being at an appropriate dilution to ensure that a sufficient number can be analyzed without too many forming into doublets, triplets, or the like.

Figure 6A:
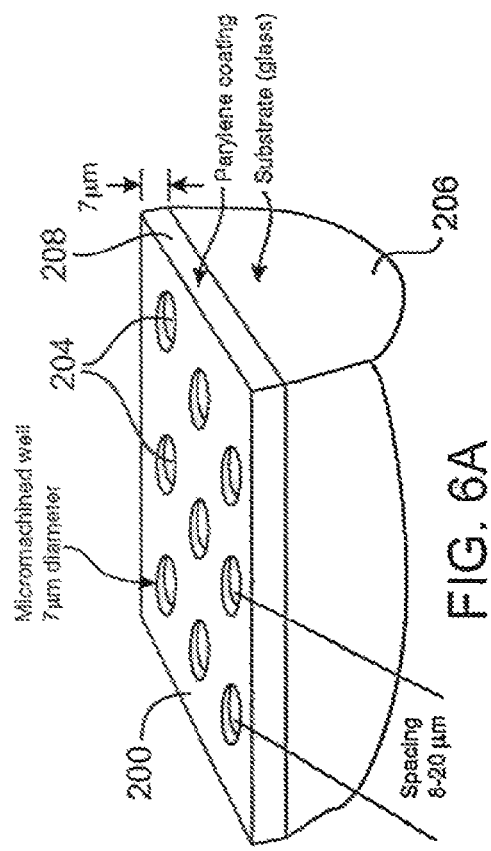
FIGS. 6A-6C schematically illustrate a plate for positioning semiconductor nanocrystal assay probes, together with a method for the use of positioned probes in multiplexed assays.
Figure 6B:
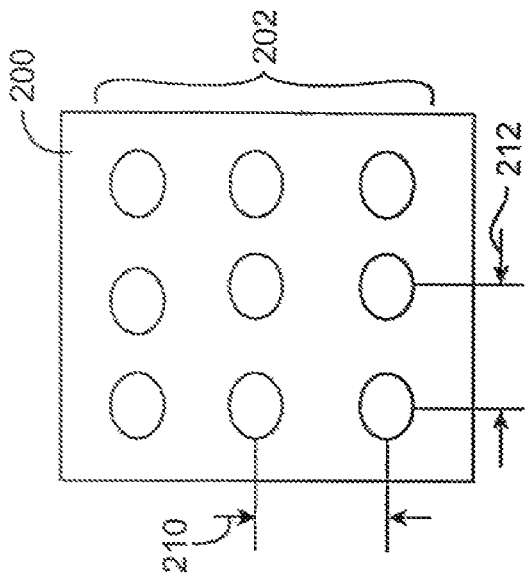
Figure 6C:
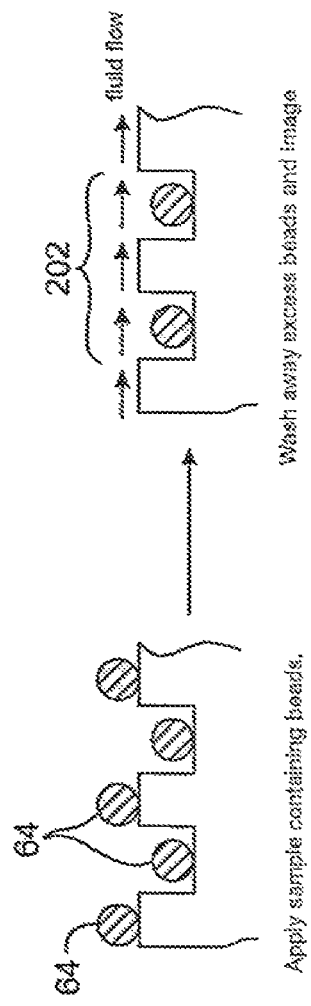

Referring now to FIGS. 6A 6C, beads can be spatially restrained and/or immobilized by a support structure 200 such as a planar surface. Typically, beads 64 will be restrained such that they are regularly spaced in a chosen geometry or array 202. The beads can be immobilized by restraining the beads in openings 204 in support structure 200, the openings optionally comprising blind holes or wells. Such wells may be fabricated by micromachining wells into the planar surface. For example, 7-micron wells that are 7 microns deep, can be created by ablating a 7 micron layer of parylene using a focused laser, and by affixing the layer on a glass surface. Other methods can be used to create microstructures on the glass surface that behave as wells, including electron beam (or other particle) drilling, mechanical drilling, masking and plasma etching, and the like.

The well dimensions may be chosen such that only a single bead is captured in the well and such that, when a lateral flow of fluid passes the beads, the single beads remain trapped in the wells (see FIG. 6C). For example, a 7-micron well may be suitable for analysis of beads from around 4 microns to 6 microns, or "monodisperse" 5 micron beads.

Other methods for capturing and spatially restraining beads include selective deposition of polymers using light-activated polymerization, where the pattern of light is determined using a photoresist. The polymers then bind non-specifically to single beads and other beads can be washed away.

More generally, support surface 200 may optionally define array 202 as a discreet array of a material capable of affixing and/or bonding to beads 64. Suitable array site materials may comprise a non-specific "sticky" surface, such as those commercially available from MOLECULAR MACHINES & INDUSTRIES, GMBH, of Heidelberg, Germany. Alternatively, the array material may comprise a specific binding moiety, a complimentary binding moiety of probes 64 typically defining a binding pair with the array material. For example, streptavidin may discreetly deposited on support structure 200 so as to define array 202, with biotinylated structures disposed on beads 64. Alternatively, streptavidin beads may specifically bind to biotinylated array sites of the support structure.

Regardless of whether array 202 is defined as a series of openings 204, or as a series of discreet bead binding sites, it will often be advantageous to dispose the support structure 200 within a fluid container, the support structure typically being affixed within at least one well of a multi-well plate. In the exemplary embodiment, support structure 200 may comprise a glass structure bonded onto the bottom of at least one well of a multi-well plate. A glass substrate 206 of support structure 200 will preferably comprise a relatively thin structure, typically being thinner than a thickness of a plate material bordering the well containing the test fluid. By using multi-well plates having a clear material bordering the wells, and limiting the thickness of a substrate 206, reading of beads 64 within openings 204 is facilitated.

Layer 208 may be affixed to substrate 206, or may alternatively be affixed directly to a surface of a multi-well plate, support structure 200 typically being deposited along the bottom surface of the well within a multi-well plate (or other test fluid containing volume) so as to allow gravity to help capture bead 64. Layer 208 may have a thickness between about half and one and one half times a size of beads 64, with openings 204 also often having a cross-sectional dimension between one half and one and one half times the size of the beads. Layer 208 may comprise a material having signal transmission characteristics which are significantly different than that of the underlying substrate or container material so as to enhance the accuracy or ease of reading the beads. Still further structures might be used to immobilize and/or position the beads, including superparamagnetic bead positioners being developed by IMMUNICON CORPORATION of Pennsylvania, and by ILLUMINA, INC. of San Diego, Calif.

In use, the mixture of spectrally encoded beads for a multiplexed assay can be deposited onto the capture surface and allowed to settle into wells by gravity or to bind to the capture surface. Excess beads are then washed away leaving single beads filling up some portion, for example, >90% of the wells or capture positions.

The captured or spatially restrained beads can then be analyzed using an imaging system as described above to capture fluorescence data at various emission wavelengths for each bead. This method provides advantages over a simple scan of randomly placed beads because (1) beads are known to be separated so the spatial resolution required for detection can be reduced (as doublets do not have to be found and rejected). This leads to greater analysis efficiency, (2) the packing of beads can be considerably higher while still retaining spatially separated singlet beads, (3) the beads do not move relative to the support and so can be scanned multiple times without concerns about movement, and (4) the concentration of beads in the sample does not need to be precise (in the random scattering approach, too high a concentration can lead to a high packing and eventually a multi-layer structure, whereas too low a concentration leads to too few beads being analyzed).

In a system where spatial and spectral information are combined by placing a coarse grating (reflection or transmission) in the emission path, such that the emitted light from each bead is spectrally dispersed in one dimension, the use of micromachined wells is particularly useful. The wells can be machined such that the dispersed images of each bead do not overlap. In addition, knowledge of the bead positions means that absolute wavelength determination can be carried out rather than relative determinations or using a spectral calibrator (See FIG. 7).

Figure 7:
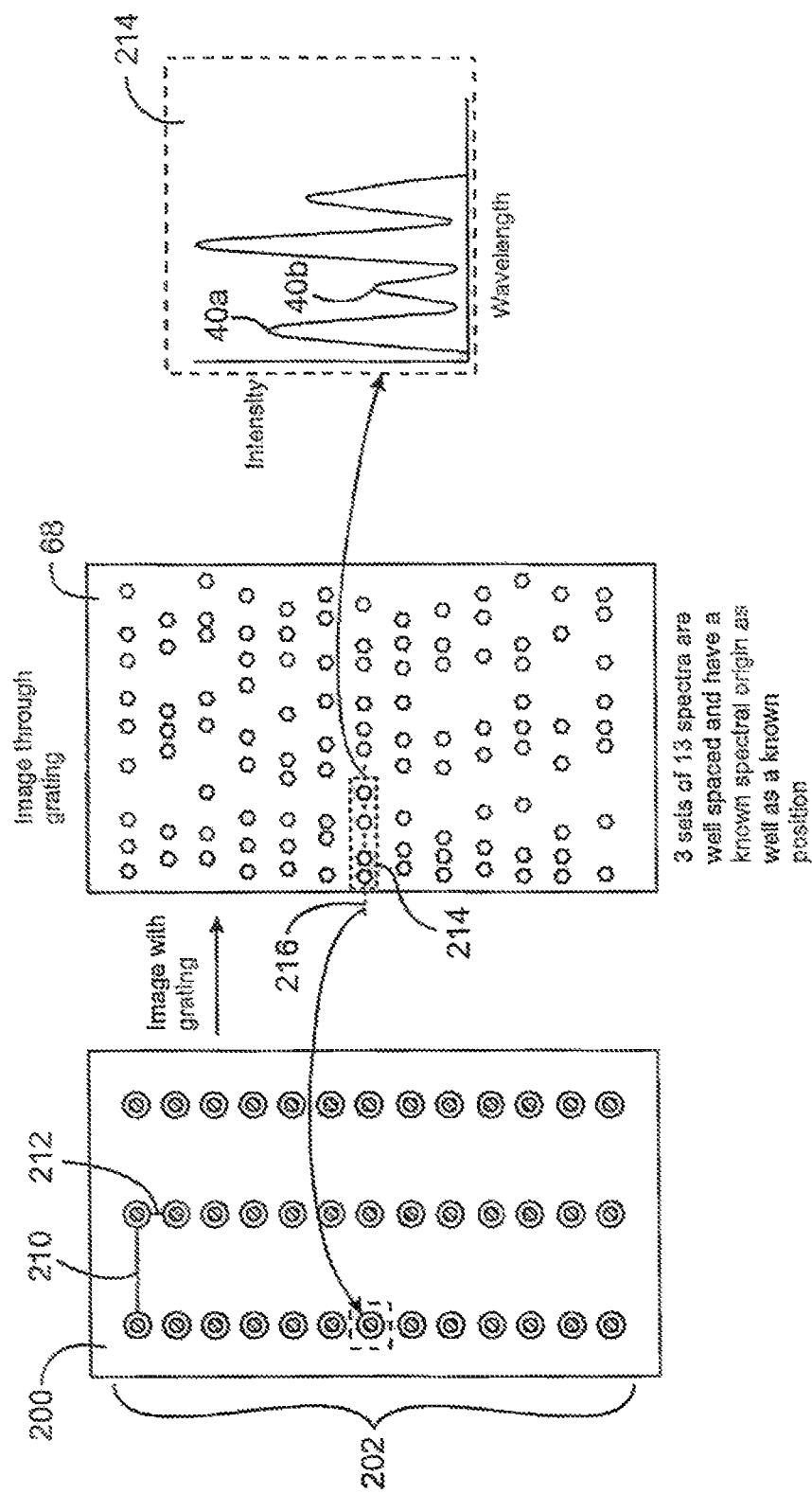
FIG. 7 schematically illustrates a method for reading the spectral labels and/or identifying assay results using the probe positioning plate of FIG. 6C.

Referring now to FIGS. 6B and 7, array 202 may have a spacing 210, 212 between array sites which is selected so as to avoid excessive overlap between spectra 214 as distributed across the imaging surface by dispersive element 54. More specifically, a spacing 210 aligned with a dispersive axis 216 of dispersive element 54 will preferably be sufficient so as to avoid any potential peak-to-peak overlap between the spectra. A spacing 212 transverse to dispersive element 216 may reduced, and/or the array pattern may be staggered so as to increase array density while still avoiding overlap among the spectra. This facilitates correlation between the dispersed spectra and the known well/bead position within array 202, as well as facilitating code interpretation.

Still further alternative bead positioning means are possible. In one variation of the positioning wells illustrated in FIGS. 6A 6C, a closely packed array of collimated holes may be distributed across a surface. Where the holes extend through a substrate defining the surface, a pressure system may be provided along an opposed surface so as to actively pull beads 64 and test fluid 32 into the array of holes. Such a system would allow a set of beads to be pulled into positioning wells, to have the assay results (optionally including bead labels and assay markers) read from the entrained beads, and then optionally, to push the beads out of the through holes. Such a positioning and reading cycle may be repeated many times to read a large number of beads within a test fluid. While there may be difficulty in transporting the beads and test fluid to the positioning surface, such a system has significant advantages.

Spectrally encoded bodies or beads may be read by a variety of differing systems. Optionally, a confocal excitation source may be scanned across a surface of a sample. Each time the excitation energy passes over an encoded bead, a fluorescence spectrum may be acquired. By raster-scanning a point excitation source in both the X and Y dimensions of a surface, all of the beads within a sample may be read sequentially. A disadvantage to such a system is that randomly arrayed beads might require scanning substantially the entire sample with quite high spatial resolution to avoid missing a single bead. This may mean that a significant amount of time is spent reading the sample surface or volume in regions that do not contain a bead. In addition, once a bead is found, it should be scanned sufficiently to ensure that the spectrum is read from a similar portion of each bead, for example, from a center of the bead. If this is not done with sufficient accuracy, it may be difficult to determine if a side of a bead, a center of the bead, or the like has been read, inhibiting accurate assay label quantitation. Such scanning is time consuming and significantly decreases the efficiency of a point scanning system. As described above, an array of wells in, for example, a slide glass may be used to organize the beads. By placing the beads in an ordered array of wells, it is unnecessary to search for each bead or to scan the beads carefully to find their centers. Rather, the array of wells is simply registered to the reader, and the reader collects spectra from the center of each well. This can greatly increase the rate of scanning, since no time is wasted searching for beads in places where they do not exist.

While the use of arrayed beads is appealing from a speed standpoint, it may involve removing a sample fluid from a test container and placing the sample in a specialized reading container structure having the wells. It would be highly desirable to be able to read the beads directly in their original container, such as in the well of a 96-well plate to avoid potential sample-to-sample cross contamination. While fabrication or modification of a standard 96-well plate is described above, it may be desirable to provide methods for restraining and/or removing beads within a fluid. It may also be desirable to have a technique that did not require one to look for beads in a region of the sample where no beads exist, while still allowing the beads to be read within a standard, unmodified 96-well plate or other standard sample holder.

Figure 8:
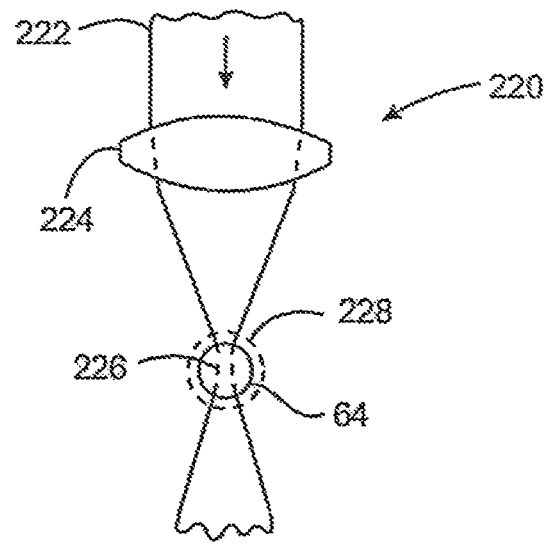
FIG. 8 schematically illustrates an energy beam for spatially restraining and optionally moving a spectrally labeled body, with the energy being used as an optical tweezers.
Figure 12:
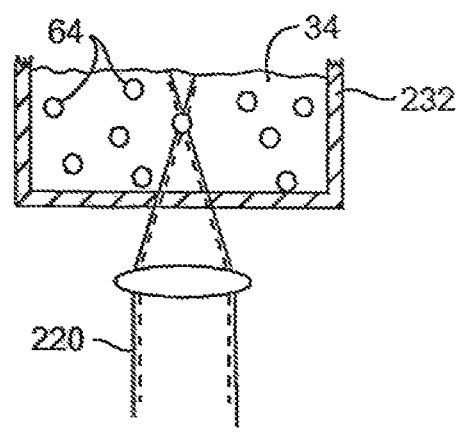
FIG. 12 schematically illustrates the selective excitation and reading of a spectrally labeled body movably disposed within a test fluid.

As can be understood with reference to FIGS. 8 12, the invention provides methods and systems for spatially restraining spectrally labeled bodies. Optical tweezers can sweep spectrally encoded beads (or any other type of bead) into an ordered array, often as the beads are read. It is not necessary to order the beads prior to reading, as they may optionally be organized as they are read.

Referring now to FIG. 8, optical tweezers 220 may comprise a laser beam 222 focused by optics 224 to a light spot or focus region 226. Optical tweezers often include a red or infrared laser beam 222, and may hold a small body, such as a spectrally labeled probe or bead, at or near the center of the point of focus.

The force used to hold a body using optical tweezers may be light pressure. Depending on the focal characteristics of optics 224, the size, intensity, and other characteristics of laser 222, and the like, a trap 228 may be defined by optical tweezers 220, with the trap capable of spatially restraining beads 64 therein. The size of trap 228 may be selected so as to limit the size and/or number of beads 64 which can be restrained therein. For example, any bead smaller than approximately 10 .mu.m in diameter that comes in contact with the focused spot 226 may be pulled into the point of highest intensity, as illustrated in FIG. 8. If this point is moved in three-dimensional space, bead 64 may be moved as well. Such movement of the bead within a moving optical tweezers is encompassed within the term "spatially restrained," as used herein. However, for beads which are larger than about one half the size of trap 228, or about 5 .mu.m in our example, only one bead can exist within trap 228 at a time. Optical tweezers are a very standard, and surprisingly simple tool, used in many different applications. See, e.g. Ashkin (1997) Proc. Natl. Acad. Sci. USA 94: 4853 4860; Helmerson et al. (1997) Olin. Chem: 43:379 383; Quake et al. (1977) Nature (London) 388:151 154; Ashkin (1972) Sci, Amer. 226:63 71; and Ashkin (1970) Phys. Rev. Lett. 24:156 159. In the exemplary embodiments, optical tweezers 220 will define a trap 228 having a dimension between about 0.1 and two times the size of bead 64, or between about 100 .mu.m and 100 .mu.m.

Figure 9:
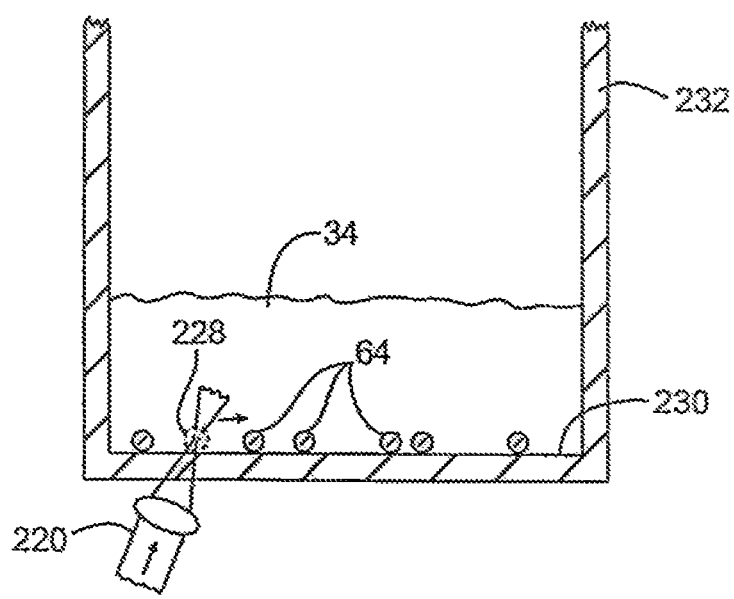
FIG. 9 schematically illustrates a method for using an energy beam to sweep along a surface of a test fluid so as to position one or more spectrally labeled beads.
Figure 11:
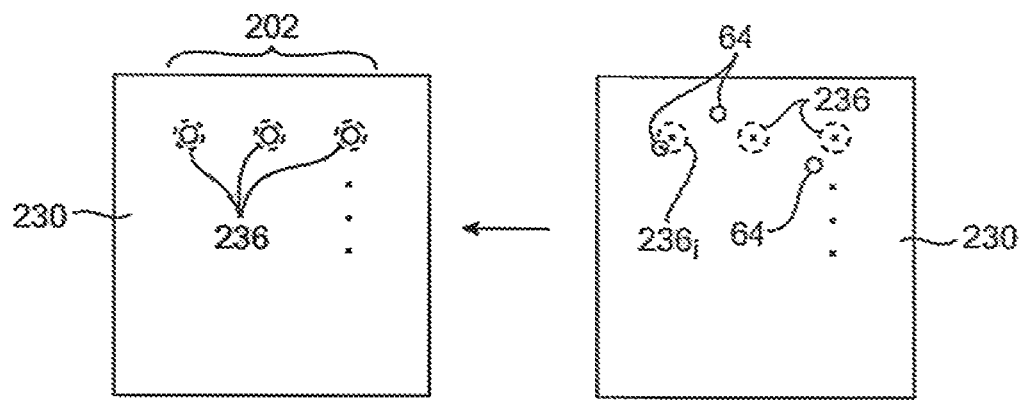
FIG. 11 schematically illustrates dynamically arraying spectrally labeled beads.

Referring now to FIGS. 9 and 11, optical tweezers 220 may be used to hold spectrally encoded beads in a moving or fixed position, and/or may be used to order them in an array 202 for reading. Tweezers 220 may be focused near a surface 230 along which beads 64 are disposed, such as near the bottom of a container 232. In the exemplary embodiment, the tweezers are focused near the bottom of a well of a multi-well plate. Beads 64 (optionally, but not necessarily being disposed within fluid 34) are moved along surface 232 array sites 236, the beads ideally being moved to the center of a detection region of a point-scanning reader. Trap 228 may be scanned along surface 230 by moving optical tweezers 220, by moving container 232 relative to the optical tweezers, by manipulating optics 224 (for example, by moving a scanning mirror with a galvanometer, or the like), or the like.

Figure 10:
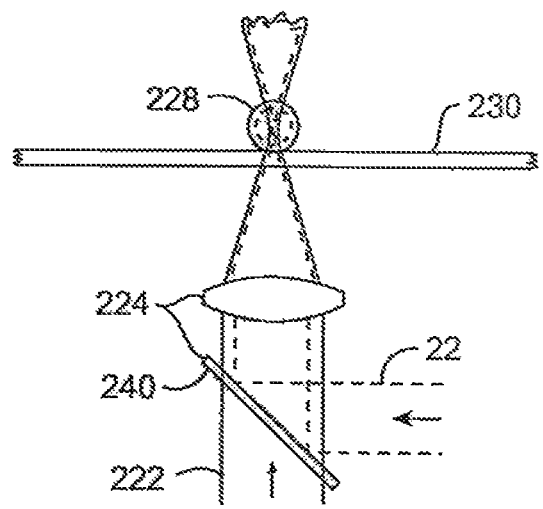
FIG. 10 schematically illustrates the use of separate energy beams for spatially restraining and generating an identifiable signal of a spectrally labeled body.

Referring now to FIG. 10, excitation energy 22 and spatially restraining energy beam 222 may optionally comprise separate energies, such as a laser beam for spatially restraining beads 64 and a filtered white light for exciting semiconductor nanocrystals of beads 64 to generate an identifiable spectrum. A dichroic mirror 240 may facilitate selectively combing energies having differing wavelengths, with the energy beams optionally being confocal, so as to define a substantially similar trap and excitation region. In the illustration of FIG. 10, the restraining energy beam and trap 228 are illustrated in solid lines, while the excitation energy and excitation region are schematically illustrated with dashed lines.

Referring now to FIG. 11, moving beads 64 relative to a surface 230 so as to prow an ordered array of beads 202 can be understood. To read all of the beads of an array 202, the scanner may efficiently be directed toward a first array site 236 and then moved directly to a second array site, and so forth, skipping the empty space in between sites. In contrast, if the disordered beads were to be point-scanned prior to ordering the array of FIG. 11, only part of one of the three illustrated beads 64 would be read, since this bead is not centered on the detection region or array site 236. This could lead to inaccurate assay results. Furthermore, after reading the first array site, the scanner might miss the remaining beads altogether, since they do not fall directly within the detection regions. Through use of optical tweezers 220 to order the array of beads, reading of a plurality of beads is greatly improved.

If optical tweezers 220 are energized and oriented at a first array site 236, an associated bead partially disposed within the array site may be pulled into the center of the trap, thereby providing an accurate quantitative measure of the assay label bead intensity by accurately alignment of a scanning system with the bead. After reading the first bead, the tweezers may be turned off to release the first bead, and the scanner may advance to the right before the tweezers are again turned on. If the scanner is moved sufficiently, retrapping of the first bead may be inhibited prior to re-energizing the scanner. Once the tweezers are turned on again, the system may be moved to the intermediate spot of the simple array illustrated in FIG. 11. While no bead may be initially present in this second array site 236, the process of scanning optical tweezers 220 may pass an adjacent bead and this bead may be trapped and brought into the intermediate array site. This second bead can then be read and released as before.

By using optical tweezers, time which might otherwise be spent looking between the scanned spots may be used more efficiently. Rather, any beads that fall in between spots may be pulled into a detection region or array site. This technique can effectively integrate the area between scanned points by bringing any beads that are disposed between the points of an intermittent array scan into the next detection region. Since only one bead may be contained in the trap at a time, such a system can significantly decrease the reading of multiple beads co-located at an array site. Conveniently, if multiple beads lie between any two points, only one bead may be trapped by the optical tweezers and read. Choosing a scan distance that corresponds to the average inter-bead spacing can decrease missing beads.

As can be understood with reference to FIG. 12, an alternative embodiment may make use of optical tweezers which are separated from the surfaces of a well. In this embodiment, the detection region remains located at the center of the trap. As the tweezers are turned on and off, the solution is mixed, so that different beads may be brought into the detection region and held while they are scanned. In other words, movement of fluid 34 relative to the reading system may optionally make use of a fixed optical tweezer and bead reading system. This technique may allow an identification or tracking system to scan a large number of beads without having to resort to precision scanning or control of the concentration of beads along a bottom or other surface of a well. Hence, such a system may be for simpler and less expensive than a system having scanning optics or the like. A similar system may restrain beads at a reading site within a flow-based system, similar to that of FIG. 5C.

In other embodiments, the optical tweezers (and more specifically, the laser beam) may be focused in a single dimension, for example, to a line (rather than being tightly focused in two dimension, for example, to a point). Such a line-focused laser may create a trap region that extends along a line, rather than being spherically centered about a single point. Such an optical tweezing system may be used to sweep or otherwise spatially restrain beads in distinct lines that can be scanned by a bead reader system having a slot aperture.

In many of the optical tweezer systems described above, the restraining energy beam may be an infrared laser, a red laser, or the like. Optionally, an infrared laser may be used which does not excite any of the semiconductor nanocrystals within a bead. In other embodiments, a red laser may be used that simultaneously traps the beads, and also excites the marker semiconductor nanocrystals so as to generate the identifiable spectrum. Optionally, the optical reading system may make use of at least a portion of the optical train of the optical tweezers. In other embodiments, the reading and restraining optical paths may be separated.

The above-described spatial restraining optical tweezers, array of openings, and the like may be used to form microarrays within a volume or surface of test structure, such as a multi-well plate for a variety of assays. For example, any array-based assay could be processed and detected within a multi-well plate without having to transfer the sample onto an array surface. Detecting signals such as fluorescence from such microarrays may be performed using any of the systems described hereinabove. For example, all of the assays processed for a single semiconductor nanocrystal pathogen detection might be performed within a well of a multi-well plate, with the panel-array printed on the bottom of each well. Related techniques are described in U.S. patent application Ser. No. 60/182,844, entitled "Single Target Counting Assays Using Quantum Dot Nanoparticles" filed Feb. 6, 2000, the full disclosure of which is incorporated herein by reference. As part of the processing, appropriate analytes may be bound to a surface within a multi-well plate, and the excess analyte removed prior to detection. This may dramatically simplify processing and detection. Other potential applications include sandwich immunoassays, DNA/RNA microarrays, surface-based molecular beacon arrays, and the like.

Specific structures for containing test fluids with beads, and/or for directing flows of such fluids and beads, may improve spectral code reading performance. Codes may be read from above, from below, or from an angle relative to vertical. Reading codes from below, for example, may be enhanced by using a fluid containing body with an opaque material over the fluid. The fluid surrounding the beads may have an index of refraction which substantially matches that of the material of the lower portion of the fluid containing body. Such structures may be particularly beneficial when reading dense bead codes.

While the exemplary embodiments of the present inventions have been described in some detail for clarity of understanding, a variety of modifications, adaptations, and changes will be obvious to those of skill in the art. Hence, the scope of the present invention is limited solely by the appended claims.

What is claimed is:

1. A method comprising:
restraining a plurality of spectrally labeled bodies with affinity binding so as to define a multiplexed array, wherein the spectrally labeled bodies are spatially resolved and comprise a plurality of fluorescent labels used to encode discrete and different emission spectra wherein each emission spectrum has a plurality of signals at differing wavelengths;
directing an image of the multiplexed array of bodies onto a sensor to sense spectra generated by the bodies; and
identifying the bodies from the spectra sensed by the sensor.

2. The method of claim 1, wherein the bodies are affixed to each other.

3. The method of claim 1, wherein the bodies are restrained within an array of openings affixed in a support structure.

4. The method of claim 1, wherein the sensor is a CCD camera.

5. A method of claim 1, wherein the spectrally labeled bodies include polymers.

6. A method of claim 1, wherein affinity binding is facilitated by a chemical moiety.

7. A method of claim 1, wherein the affinity binding is specific.

8. A method of claim 1, wherein the plurality of signals include a reference signal.

9. A method of claim 1, wherein the affinity binding is facilitated with a binding pair.

10. The method of claim 1, wherein the bodies are restrained to a support structure.

11. The method of claim 1, wherein the bodies are restrained in the multiplexed array by an array of discrete binding sites.

12. A method of claim 8, wherein the reference signal identifies a spectral code family.

13. A method of claim 9, wherein one member of the binding pair is affixed to at least one of the plurality of spectrally labeled bodies and the other member is affixed to a site of the multiplexed array.

14. The method of claim 10, wherein the support structure has a substantially planar surface.

15. The method of claim 10, wherein the support structure contains a plurality of openings sized to accommodate one of the spectrally labeled bodies.

16. The method of claim 10, wherein a plurality of unbound bodies are washed away.

17. A method of claim 11, wherein the discrete binding sites are arranged so as to inhibit a presence of more than a single body at each binding site.

18. A method of claim 11, wherein the binding sites comprise a material capable of binding to the bodies.

19. A method of claim 18, wherein the material comprises a selective affinity molecule which selectively binds to one or more particular bodies.

20. The method of claim 19, wherein the selective affinity molecule is streptavidin.

21. The method of claim 19, wherein a selective binding material is a biotinylated structure.

* * * * *